US008911362B2

(12) United States Patent
Kaneko

(10) Patent No.: US 8,911,362 B2
(45) Date of Patent: Dec. 16, 2014

(54) ENDOSCOPE

(75) Inventor: Hiroyuki Kaneko, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/618,412

(22) Filed: Sep. 14, 2012

(65) Prior Publication Data

US 2013/0012781 A1 Jan. 10, 2013

Related U.S. Application Data

(63) Continuation of application No. PCT/JP2012/060443, filed on Apr. 18, 2012.

(30) Foreign Application Priority Data

Apr. 28, 2011 (JP) ................................. 2011-101296

(51) Int. Cl.
*A61B 1/00* (2006.01)
*A61M 31/00* (2006.01)
*A61M 37/00* (2006.01)
*A61M 25/00* (2006.01)
*G01N 21/00* (2006.01)
*A61B 1/005* (2006.01)

(52) U.S. Cl.
CPC ......... *A61B 1/00078* (2013.01); *A61B 1/00066* (2013.01); *A61B 1/0052* (2013.01); *A61B 1/0057* (2013.01)
USPC ........... 600/148; 600/146; 600/147; 600/149; 600/150; 604/95.04; 604/528; 356/241.6

(58) Field of Classification Search
CPC .... A61B 1/005; A61B 1/0051; A61B 1/0052; A61B 1/0055; A61B 1/0056; A61B 1/0057
USPC ......... 600/139–152, 104, 106, 107, 114, 115, 600/131, 434, 435, 585; 604/95.01–95.05, 604/523–528; 606/1; 356/241.1–241.6
See application file for complete search history.

(56) References Cited

FOREIGN PATENT DOCUMENTS

| JP | 2005-160790 | | 6/2005 | |
|---|---|---|---|---|
| JP | 2005-160791 | | 6/2005 | |
| JP | 2005160791 A | * | 6/2005 | ............... A61B 1/00 |
| JP | 2008-264108 | | 11/2008 | |

* cited by examiner

*Primary Examiner* — Ryan Henderson
(74) *Attorney, Agent, or Firm* — Scully, Scott, Murphy & Presser, P.C.

(57) ABSTRACT

An endoscope including a bending operation apparatus including a bending operation mechanism section and a bending portion braking mechanism section in an operation section, the bending operation mechanism section includes a bending lever, a first bearing member transmitting a force of the lever, and a cylindrical member rotated with an operation of the lever, and the bending portion braking mechanism section includes a bending state keeping lever, a braking shaft body transmitting a force of the lever, a second bearing member pivotally supporting the braking shaft body, a rotation pressing member rotating around an axis of the second bearing member, and having inclined projection portions, a slide pressing member having inclined projection portions opposed to the projection portions, a friction member abutting on the cylindrical member, a regulation member regulating a gap where the friction member is disposed, and positioning members regulating a braking force of the friction.

7 Claims, 23 Drawing Sheets

ENDOSCOPE

CROSS REFERENCE TO RELATED APPLICATION

This application is a continuation application of PCT/JP2012/060443 filed on Apr. 18, 2012 and claims benefit of Japanese Application No. 2011-101296 filed in Japan on Apr. 28, 2011, the entire contents of which are incorporated herein by this reference.

BACKGROUND OF THE INVENTION

1. Field of the Invention

The present invention relates to an endoscope that includes a bending portion braking mechanism section which keeps a bending state of a bending portion which is bent, in a bending operation mechanism section which bends the bending portion.

2. Description of the Related Art

Conventionally, endoscopes which are capable of performing observation and various kinds of treatments by inserting elongated insertion portions into bodies have been used. In the endoscopes, some endoscopes include bending portions in insertion portions for the purpose of performing observation by directing observation optical systems contained in distal end portions of the insertion portions to the directions of objects, or for the purpose of facilitating insertion into sites to be examined.

A bending portion includes, for example, a bending portion set configured in such a manner that a plurality of bending pieces are connectively provided rotatably to be bent in two vertical directions or four vertical and lateral directions. Distal ends of bending wires corresponding to the respective bending directions are fixed to a most distal end bending piece of the bending portion set.

According to a configuration, for example, a surgeon pulls a desired bending wire via a bending operation apparatus, and thereby can bend the bending portion in a desired direction. An operation section that is also used as a grasping portion is included at a proximal end side of the insertion portion of an endoscope. A bending operation apparatus is provided in the operation section.

For example, Japanese Patent Application Laid-Open Publication No. 2005-160791 shows an endoscope in which a vertical bending operation lever and a lateral bending operation lever are respectively pivotally supported at both left and right side surfaces of an operation section main body that configures an operation section. In the endoscope, finger rest portions of the respective operation levers extend to a top surface side region of the operation section, and the respective finger rest portions are disposed laterally side by side above the operation section main body.

Further, in the endoscope, a bending lock lever as a bending portion braking mechanism section for keeping a bending state of the bending portion is pivotally supported at both left and right side surface regions of the operation section main body. A finger rest portion of the bending lock lever is disposed on a bottom surface side of the operation section main body which is a region where a forefinger of a grasping hand is naturally located when a surgeon grasps a grip portion with one hand.

Accordingly, the surgeon can properly perform an operation of the vertical bending operation lever which is placed at the operation section main body, an operation of the lateral bending operation lever, or an operation of the bending lock lever with one hand which grasps the operation section.

The bending portion braking mechanism section of the endoscope is configured by including a bending lock lever, a shaft body, a braking regulating plate, a first cam, a second cam, and a friction member. The shaft body is configured to rotate integrally with the bending lock lever. The braking regulating plate is made of a resin with slippage taken into consideration. The first cam is configured by a metal disk which rotates with rotation of the shaft body, and includes a mountain-shaped braking projection portion. The second cam is configured by a metal disk which is disposed without rotating, and includes a mountain-shaped braking projection portion. The friction member is made of a resin, and is moved and pressed against a pulley by the braking projection of the first cam and the braking projection of the second cam being overlaid on each other.

In the bending portion braking mechanism section, a projecting amount of a regulating screw which supports the braking regulating plate is changed, whereby regulation of the braking force of the bending portion braking mechanism section can be performed.

In the endoscopes of recent years, the kind and the amount of the components contained in the endoscopes which are inserted into the insertion portions have increased with high functionality. Therefore, bending force amounts at a time of bending the bending portions become large, and fixing force amounts for keeping the bending states of the bending portions become large.

SUMMARY OF THE INVENTION

An endoscope according to one aspect of the present invention is an endoscope including an insertion portion having a bendable bending portion, and an operation section connectively provided at a proximal end side of the insertion portion, and including, in the operation section, a bending operation apparatus which is operated when the bending portion is caused to perform a bending operation, wherein the bending operation apparatus includes a bending operation mechanism section and a bending portion braking mechanism section, the bending operation mechanism section includes a bending lever which is rotatably disposed at an operation section main body of the operation section, and is rotated when the bending portion is caused to perform a bending operation, a first bearing member that pivotally and rotatably supports a bending operation shaft body which has the bending lever integrally fixed to one end, and transmits a rotation force of the bending lever, and is fixed to a support panel integral with the operation section main body, and a cylindrical member that is fixedly provided integrally at the other end of the bending operation shaft body, is rotated with rotational operation of the bending lever, and pulls and loosens an operation wire which is disposed in an outer circumferential groove, and the bending portion braking mechanism section includes a bending state keeping lever that is rotatably disposed at the operation section main body of the operation section, and is operated when a bending state of the bending portion which is bent is kept, a braking shaft body that has the bending state keeping lever integrally fixed to one end, and transmits a rotation force of the bending state keeping lever, a second bearing member that pivotally and rotatably supports the braking shaft body, and is fixed to the support panel, a rotation pressing member that is rotatably disposed in the first bearing member, rotates around an axis of the second bearing member with a rotational operation of the braking shaft body, and has a plurality of inclined projection portions at a peripheral portion of an outside side surface, a slide pressing member that is disposed slidably in an axial direction of the first bearing member, and has a plurality of inclined projection portions opposed to the inclined projection portions of the rotation pressing member, at a peripheral portion of an inside side surface, a friction member that is slidable in the axial direction of the first bearing member, is disposed between the slide pressing member and the cylindrical member, and is capable of abutting on the cylindrical member, a regulation member that is disposed at an outside side surface of the support panel, is slidable in the axial direction of the first bearing member, and is capable of regulating a gap in which the rotation pressing member, the slide pressing member and the friction member are disposed, and a plurality of positioning members that are disposed at the support panel by screwing, separate the regulation member from the support panel by changing an abutment state on the regulation member, and regulate a braking force of the friction member to the cylindrical member.

BRIEF DESCRIPTION OF THE DRAWINGS

FIG. 21 is a view explaining an elastic contact point which is included by a conductive metal body disposed in electrical contact with an end surface of a first corrugated tube pipe sleeve of the light guide connector;

FIG. 22 is a view explaining configurations of a frame member also used as a shield case and the conductive metal body;

FIG. 24 is a view seen from the direction of the Y24-Y24 line of FIG. 23;

FIG. 25 is a view seen from the direction of the Y25-Y25 line of FIG. 23;

DETAILED DESCRIPTION OF THE PREFERRED EMBODIMENT

Hereinafter, an embodiment of the present invention will be described with reference to the drawings.

Figure 1:
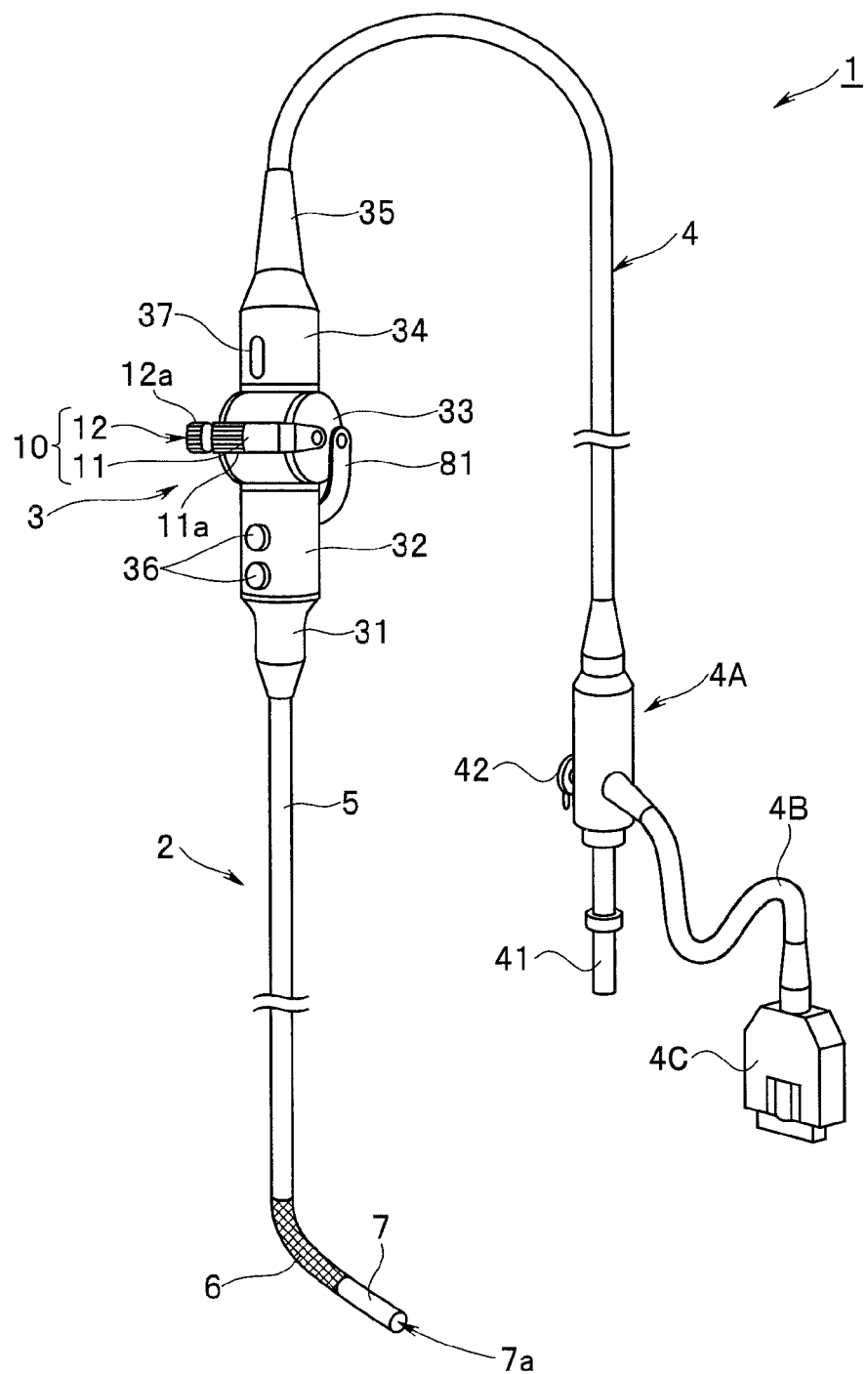
FIG. 1 is a view relating to an endoscope of one embodiment of the present invention, and explaining the endoscope that includes a bending portion which is bendable, a bending operation mechanism section which bends the bending portion, and a bending portion braking mechanism section which keeps a bending state of the bending portion.

As shown in FIG. 1, an endoscope 1 is configured by including an elongated insertion portion 2, an operation section 3 and a universal cord 4. The operation section 3 is connectively provided at a proximal end of the insertion portion 2. The universal cord 4 is extended from a proximal end side portion of the operation section 3. The universal cord 4 is configured as a flexible tubular member having a sufficiently long length as compared with the insertion portion 2.

The insertion portion 2 is configured by a rigid portion 5, a bending portion 6 and a distal end portion 7 being connectively provided in sequence from the operation section 3 side. The endoscope 1 of the present embodiment includes the rigid portion 5 at the insertion portion 2, and is suitable to be inserted into a body through a guide pipe such as a trocar which is tapped into an abdominal wall, for example.

The endoscope may be an endoscope with a soft insertion portion by including a flexible tube portion which is soft and has flexibility instead of the rigid portion 5.

An image pickup window (not illustrated) and an illuminating window (not illustrated) configuring an observation section are provided at a distal end surface 7a of the distal end portion 7. An image pickup optical system having an objective lens and the like is faced to a proximal end surface of the image pickup window. A distal end face of a light guide fiber bundle is faced to a proximal end surface of the illuminating window. In the distal end portion 7, the objective lens not illustrated, an image pickup device such as a CCD, and a C-MOS disposed at an image forming position of the objective lens are provided.

The bending portion 6 is configured to be bendable in a vertical direction and a lateral direction. The bending portion 6 is bent by a bending operation apparatus 10 provided at the operation section 3. The endo scope 1 of the present embodiment includes a vertical bending operation mechanism section 10A and a lateral bending operation mechanism section 10B which will be described later.

More specifically, the bending portion 6 bends in a vertical direction with an operation of a vertical bending operation lever (hereinafter, abbreviated as a vertical lever) 11 which is a bending operation body of the vertical bending operation mechanism section 10A. Further, the bending portion 6 bends in a lateral direction with an operation of a lateral bending operation lever (hereinafter, abbreviated as a lateral lever) 12 which is a bending operation body of the lateral bending operation mechanism section 10B.

Figure 2:
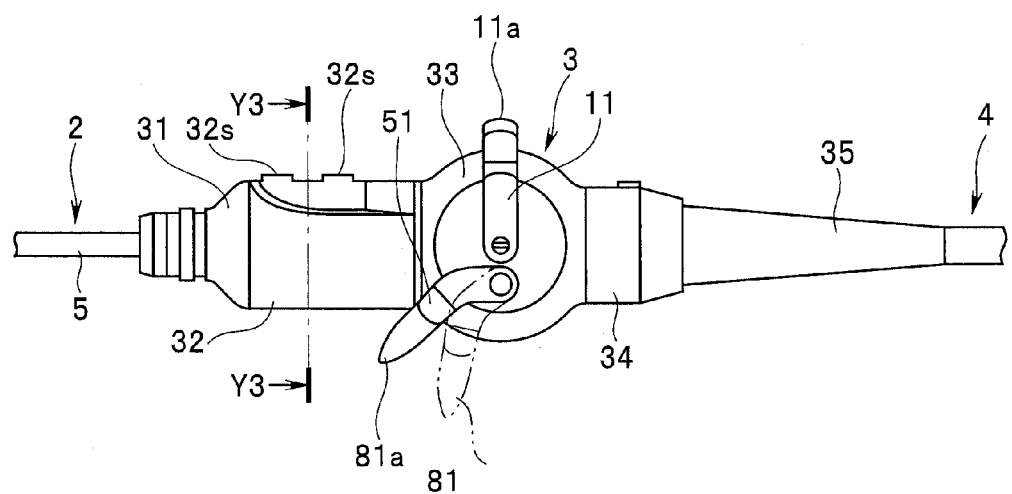
FIG. 2 is a view explaining a configuration of an operation section including a bending operation lever and a bent state keeping lever.

As shown in FIG. 1 and FIG. 2, the operation section 3 is mainly configured by a fixing ring portion 31, an auxiliary grip portion 32, an operation section main body 33, a main grip portion 34 and a connection member 35 being connectively provided from the insertion portion side. The operation section 3 is in a quasi-cylindrical shape as a whole.

The fixing ring portion 31 connects a distal end side of the operation section 3 and the proximal end side of the insertion portion 2.

The auxiliary grip portion 32 is disposed at a distal end side of the operation section main body 33, and includes a remote switch 32s and the like which control the image pickup device and the like of the observation portion 7a.

The operation section main body 33 contains a bending portion operation mechanism section such as a bending wire and a pulley not illustrated in an interior thereof, and the vertical lever 11, the lateral lever 12 and a bending state keeping lever (hereinafter, abbreviated as an engage lever) 81 are placed at an exterior thereof. The engage lever 81 configures a bending portion braking mechanism section 80 which will be described later.

The main grip portion 34 is disposed at a proximal end side of the operation section main body 33. The connection member 35 in a tapered shape having flexibility is connected to a proximal end side of the main grip portion 34. The universal cord 4 extended from the operation section 3 is covered with the connection member 35 in the tapered shape so that an end portion of the universal cord 4 is prevented from being buckled when the end portion of the universal cord 4 is bent in a vicinity of the main grip portion 34.

In the insertion portion 2, in the operation section 3 and in the universal cord 4 of the endoscope 1, a plurality of components contained in the endoscope such as the light guide fiber bundle, a signal cable which transmits various signals, a shield cable and various tubes are inserted.

A light guide connector 4A is provided at an extended end of the universal cord 4. The connector 4A is connectable to a light source apparatus which is an outside apparatus not illustrated. The light guide connector 4A is provided with a light guide pipe 41 and a vent pipe sleeve 42.

In the light guide connector 4A, a camera cable 4B branches from a side surface thereof. An image pickup connector 4C is provided at an extended end of the camera cable 4B. The connector 4C is electrically connected to a control apparatus which is an outside apparatus not illustrated or a camera control unit including a signal processing circuit.

The vertical lever 11 provided at the operation section main body 33 is a lever for pulling and loosening the vertical bending wire which is an operation wire (see reference sign 18 of FIG. 7) which is provided in the operation section main body 33. Meanwhile, the lateral lever 12 is a lever for pulling and loosening the lateral bending wire which is provided in the operation section main body 33.

In the present embodiment, one end portion of the vertical lever 11 is pivotally supported rotatably at a right side surface portion of the operation section main body 33, and one end portion of the lateral lever 12 is pivotally supported rotatably at a left side surface portion of the operation section main body 33. A center of rotation of the vertical lever 11 and a center of rotation of the lateral lever 12 correspond to each other in the same straight line which laterally penetrates through the operation section main body 33.

In the present embodiment, the levers 11, 12 or the like rotating around an axis in a clockwise direction or around an axis in a counterclockwise direction is described as rotation.

Figure 3:
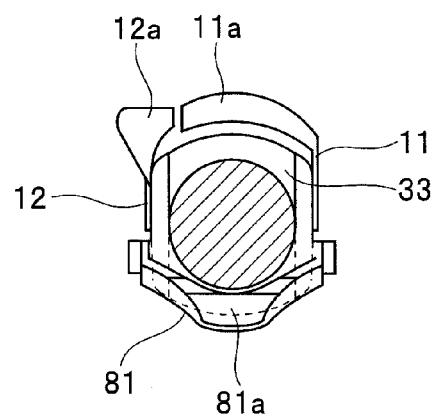
FIG. 3 is a view explaining disposition positions of an auxiliary grip portion, a vertical bending operation lever, a lateral bending operation lever and a bending state keeping lever, seen from the direction of the Y3-Y3 line of FIG. 2.

As shown in FIG. 1 to FIG. 3, a finger rest portion 11a for operation included by the vertical lever 11 and a finger rest portion 12a for operation included by the lateral lever 12 are disposed laterally side by side on a top surface side of the operation section main body 33. An up index 34u of the main grip portion 34 is attached to a position corresponding to the top surface side of the operation section main body 33 and notifies a surgeon of an upper side orientation of the operation section 3.

Figure 4:
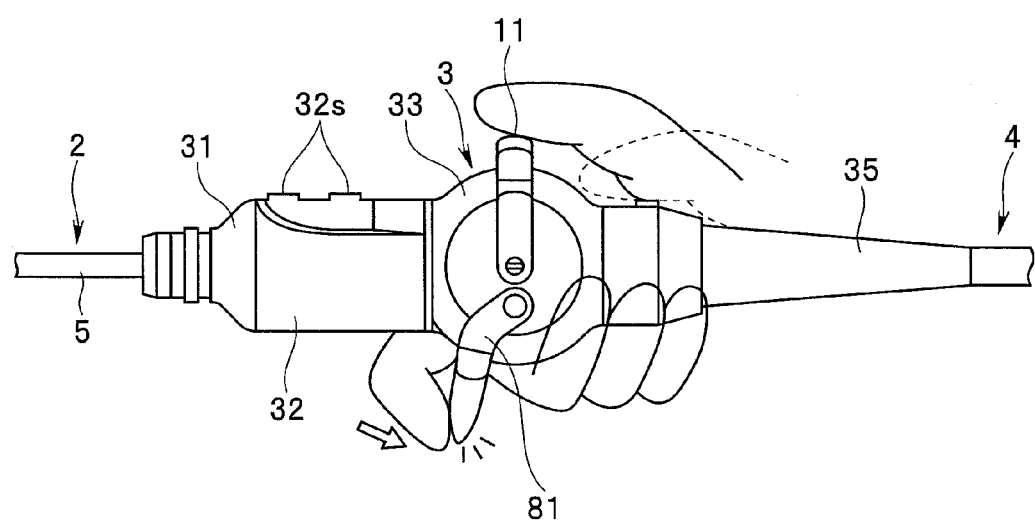
FIG. 4 is a view explaining a grasping operation example of the operation section of the endoscope.

As shown in FIG. 3 and FIG. 4, the finger rest portion 11a for operation and the finger rest portion 12a for operation are disposed in a region where a thumb of one hand of the surgeon who grasps the main grip portion 34 is naturally located with respect to the operation section main body 33, that is, an upper side of the operation section main body 33.

The operation section main body 33 is provided with an engage lever 81 which is a braking operation body of the bending portion braking mechanism section 80. One end portion and the other end portion of the engage lever 81 are pivotally supported at predetermined positions on both left and right side surfaces of the operation section main body 33 respectively.

In an intermediate portion of the engage lever 81, a finger rest portion 81a for operation is included. The finger rest portion 81a for operation of the engage lever 81 is disposed in a region where a forefinger of a hand is naturally located with respect to the operation section main body 33 when a surgeon grasps the main grip portion 34 with one hand as described above, that is, at a lower side of the operation section main body 33.

According to the configuration, the surgeon can easily perform an operation of the levers 11 and 12 placed at the operation section main body 33 with a thumb of the hand grasping the operation section 3, while the surgeon can easily perform an operation of the engage lever 81 placed at the operation section main body 33 with the forefinger or the like of the grasping hand. In addition, the operation section 3 is also applicable to grasping by either a right hand or a left hand.

Here, with reference to FIG. 5 to FIG. 7, the bending operation mechanism section which is incorporated in the operation section main body 33 will be described.

Figure 5:
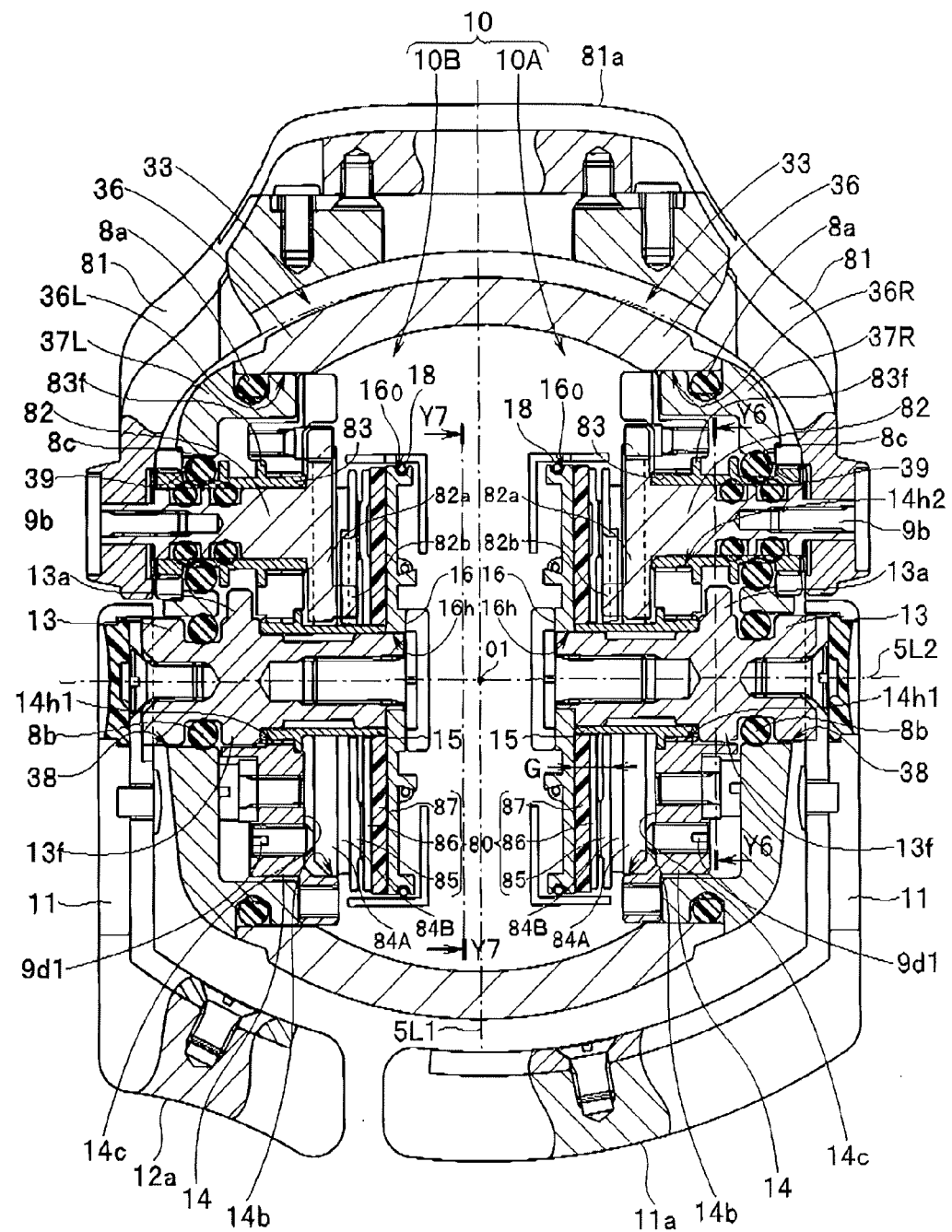
FIG. 5 is a view explaining a configuration of a bending operation mechanism section including a bending portion braking mechanism section provided in an operation section main body of the endoscope.

As shown in FIG. 5, in the operation section main body 33, the bending operation mechanism sections 10A and 10B including the bending portion braking mechanism sections 80 are provided.

The bending operation apparatus 10 is configured by including the vertical bending operation mechanism section 10A and the lateral bending operation mechanism section 10B. The vertical bending operation mechanism section 10A is disposed in a region at a right side of a straight line 5L1 shown by a dashed line passing through a center $O_1$ of the operation section main body 33, and the lateral bending operation mechanism section 10B is disposed in a region at a left side of the straight line 5L1. The respective bending operation mechanism sections 10A and 10B respectively include the bending portion braking mechanism section 80.

In the following description, a center O1 side of a line segment 5L2 which intersects the straight line 5L1 at the center $O_1$ is described as an inside, and an outer side of the operation section main body 33 is described as an outside.

The operation section main body 33 is configured by including a case body 36, and a pair of opening blocking covers 37R and 37L. In the case body 36, a right side opening 36R and a left side opening 36L are formed. The opening blocking covers 37R and 37L are in cylindrical shapes.

The right side opening blocking cover 37R is integrally assembled to the right side opening 36R, and the left side opening blocking cover 37L is integrally assembled to the left side opening 36L. A gap between an inner surface of the opening 36R and an outer periphery of the opening blocking cover 37R, and a gap between an inner surface of the opening 36L and an outer periphery of the opening blocking cover 37L are liquid-tightly sealed by seal rings 8a.

The bending operation mechanism sections 10A and 10B including the bending portion braking mechanism sections 80 shown in FIG. 5 are configured to be in an enantiomorphic relation laterally symmetrical with respect to the straight line 5L1. Accordingly, the configurations of the bending operation mechanism sections 10A and 10B do not differ from each other in principle.

Therefore, the same reference signs are assigned to the constituent elements of the vertical bending operation mechanism section 10A and the lateral bending operation mechanism section 10B, and only the configuration of the vertical bending operation mechanism section 10A will be described, whereas the description of the lateral bending operation mechanism section 10B will be omitted.

The bending operation mechanism section 10A is configured by mainly including the vertical lever 11, a bending operation shaft body (hereinafter, abbreviated as a first shaft body) 13, a support panel 14, a first bearing member 15, a pulley 16, a stopper frame 17, and an operation wire 18.

In a side surface of the opening blocking cover 37R to be a right side surface portion of the operation section main body 33, a first through-hole 38 and a second through-hole 39 are formed. The support panel 14 is integrally fixed to an opening end and an opening inner wall surface of the opening blocking cover 37R. The support panel 14 is made of a metal and in a disk shape.

The first through-hole 38 is a hole through which the first shaft body 13 is inserted. The first through-hole 38 is formed in a center of the side surface of the opening blocking cover 37R. A gap between an inner surface of the first through-hole 38 and an outer periphery of the first shaft body 13 is liquid-tightly sealed by a seal ring 8b.

The first shaft body 13 which passes through the first through-hole 38 is disposed and pivotally supported in the first bearing member 15 in a cylindrical shape. The first bearing member 15 is integrally fixed in a first through-hole 14h1 which is formed in the support panel 14.

The first shaft body 13 includes a flange 13f in a central portion in a longitudinal direction. An inside end surface of the flange 13f is positioned by abutting on an outside end surface of the first bearing member 15. In the positioned state, an inside protruded portion at an inside from the flange 13f of the first shaft body 13 is fitted in the first bearing member 15. The inside protruded end portion protrudes by a predetermined length from the inside end surface of the first bearing member 15.

Reference sign 13a designates a projection. The projection 13a is projectingly provided at an outer side by a predetermined length from an outer circumferential face of the flange 13f.

The pulley 16 is a cylindrical member, and is locked and fixed to the inside protruded end portion of the first shaft body 13 which is protruded from the inside end surface of the first bearing member 15. In order to lock and fixed the first shaft body 13 and the pulley 16, the inside protruded end portion in an odd shape and having a cutout portion is formed on a circumferential surface of the inside protruded end portion of the first shaft body 13, and an oddly-shaped hole 16h in which the inside protruded end portion in the odd shape is disposed is formed at the pulley 16 side.

According to the configuration, the inside protruded end portion of the first shaft body 13 is fitted in the hole 16h of the pulley 16 and the oddly-shaped portions are engaged with each other, whereby both the hole 16h and the inside protruded end portion are configured to rotate integrally. The odd shape means the shape in which both the portions integrally rotate when both the portions are engaged with each other, and indicates a shape other than a circular shape.

Further, a stop screw 9a which prevents the pulley 16 from falling from the first shaft body 13 is screwed onto the inside protruded distal end of the first shaft body 13. In the screwed state, the pulley 16 is prevented from falling in an axial direction of the first bearing member 15, and is positioned to the inside end surface of the first bearing member 15. In addition, the first shaft body 13 and the first bearing member 15 are also retained and positioned in the axial direction with respect to the first bearing member 15 by the inside end surface of the flange 13f.

As a result, the first shaft body 13 is rotatably supported in the state in which the first bearing member 15 fixed to the support panel 14 is positioned in the axial direction.

Figure 6:
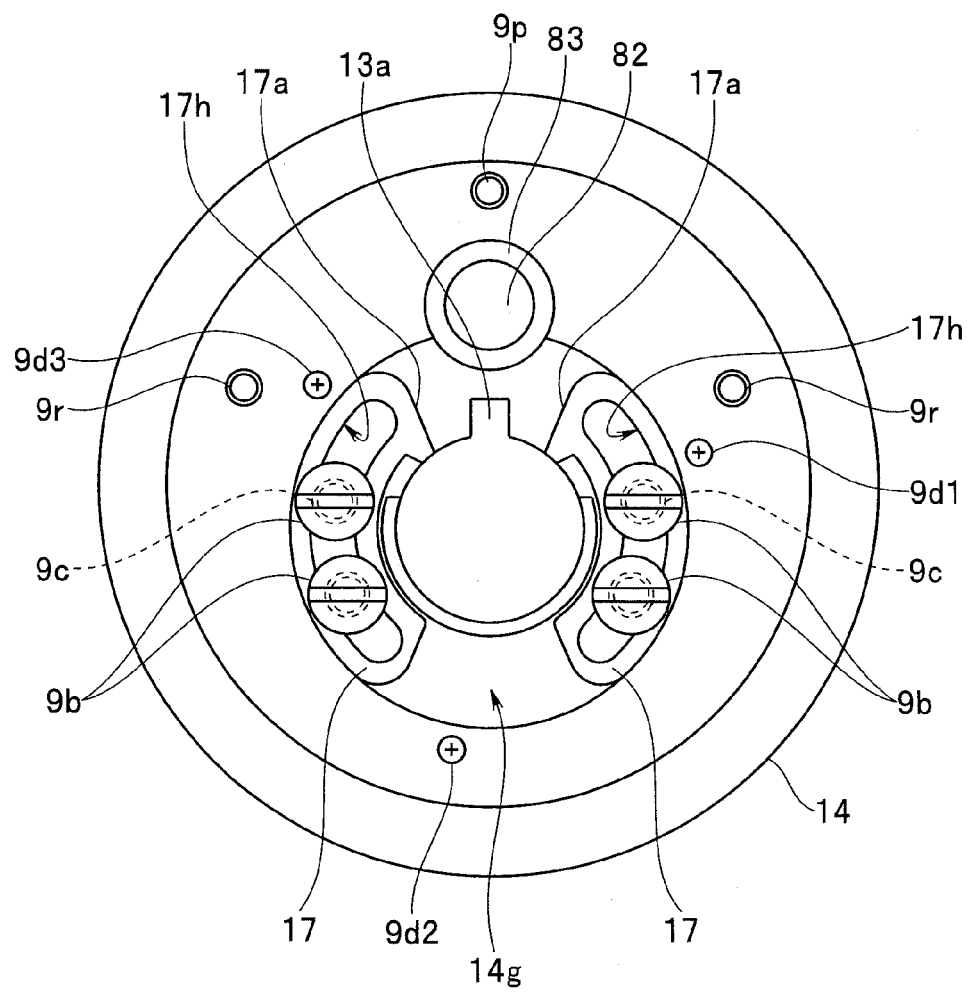
FIG. 6 is a view of an outside side surface of a support panel seen from the direction of the Y6-Y6 line of FIG. 5.

A ring-shaped circumferential groove 14g shown in FIG. 6 is formed in a periphery of the first through-hole 14h1, at an outside end side of the support panel 14. In the circumferential groove 14g, a pair of stopper frames 17 which is means that defines the rotation region of the vertical lever 11 is movably placed.

The stopper frame 17 is formed into a predetermined shape so as to move in the circumferential groove 14g. The stopper frame 17 includes an abutment surface 17a which defines a terminal end of the projection 13a which moves with rotation of the first shaft body 13. The stopper frame 17 is integrally fixed into the circumferential groove 14g by, for example, screwing. A long hole 17h through which a screw portion of a fixing screw 9b is inserted is formed in the stopper frame 17. Meanwhile, at a predetermined position of the circumferential groove 14g, female screws 9c in which the screw portions of the fixing screws 9b are screwed are formed.

According to the configuration, a pair of stopper frames 17 are respectively disposed at desired positions in the circumferential groove 14g, and thereafter, are integrally fixed by the fixing screws 9b being screwed thereon. As a result, setting of a stop position, and regulation of the stop position of the projection 13a are freely performed. More specifically, regulation of a rotation amount of the vertical lever 11 can be freely performed.

Reference sign 82 designates a braking shaft body (hereinafter, abbreviated as a second shaft body) which will be described later, and reference sign 83 designates a second bearing member which will be described later. Reference signs 9d1, 9d2 and 9d3 are regulating screws which will be described later as positioning members.

Figure 7:
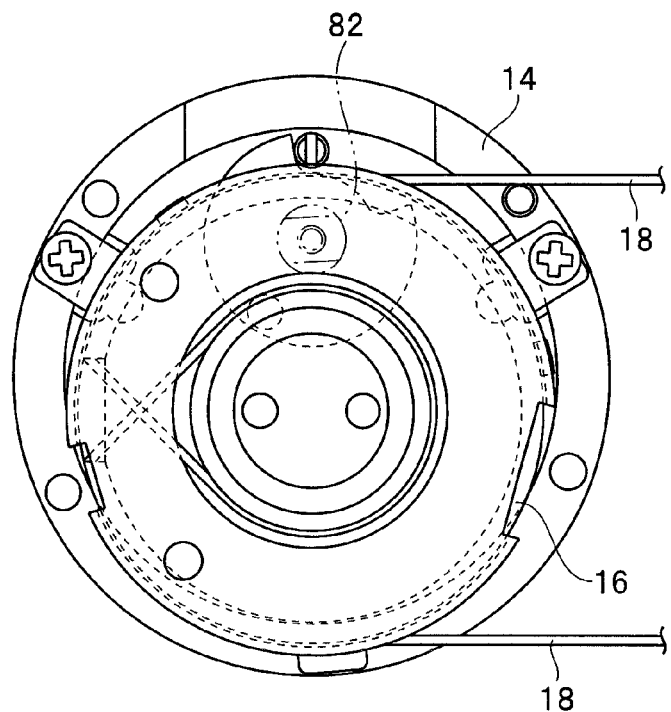
FIG. 7 is a view of the bending operation mechanism section including the bending portion braking mechanism section seen from the direction of the Y7-Y7 line of FIG. 5.

As shown in FIG. 5 and FIG. 7, the operation wires 18 corresponding to the vertical direction are disposed by being wound around an outer circumferential groove 16o of the pulley 16. One end portion of each of the operation wires 18 is fixed to the pulley 16. The other end portion of each of the operation wires 18 is guided into the insertion portion 2 from the pulley 16, and is fixed to a predetermined position of the bending portion 6.

With the rotational operation of the vertical lever 11 of the bending operation mechanism section 10A described above, the pulley 16 integral with the first shaft body 13 rotates. The bending portion 6 is configured to bend by the operation wire 18 being pulled and loosened with the rotation of the pulley 16.

Next, with reference to FIG. 5 and FIG. 8 to FIG. 13, the bending portion braking mechanism section 80 will be described.

The bending portion braking mechanism section 80 is configured by mainly including an engage lever 81, a second shaft body 82, a second bearing member 83, a braking regulating plate 84, a first cam 85, a second cam 86 and a friction member 87.

In the present embodiment, the braking regulating plate 84 is a regulating member, and is configured by including a first braking plate 84A configuring a first layer, and a second braking plate 84B configuring a second layer.

As shown in FIG. 5, the second through-hole 39 is provided by being separated by a predetermined distance in a predetermined direction from the first through-hole 38. The second through-hole 39 is a hole through which the second bearing member 83 is inserted. A gap between an inner surface of the second through-hole 39 and an outer periphery of the second bearing member 83 is liquid-tightly sealed by a seal ring 8c.

An inside end portion of the second bearing member 83 in a cylindrical shape is integrally fixed into a second through-hole 14h2 of the support panel 14. The second bearing member 83 includes a flange 83f in a central portion. The inside end portion of the second bearing member 83 is positioned and disposed in the second through-hole 14h2 by an inside end surface of the flange 83f abutting on an outside end surface of the support panel 14.

In the positioned state, the inside end portion of the second bearing member 83 protrudes by a predetermined amount from a bottom surface 14c of a bore 14b which is formed in an inside of the support panel 14. A depth of the bore 14b is set at a predetermined dimension.

Figure 8:
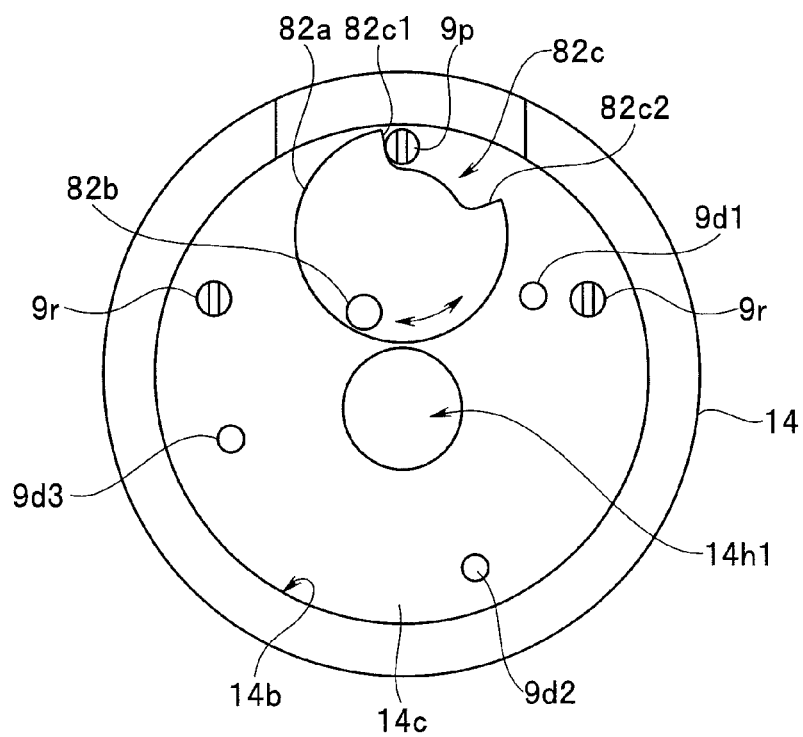
FIG. 8 is a view explaining a configuration of an inside side surface of the support panel.

The second shaft body 82 is disposed and pivotally supported in the second bearing member 83. A ring portion 82a shown in FIG. 5 and FIG. 8 is integrally provided at an inside end surface of the second shaft body 82. From the inside end surface of the ring portion 82a, a convex portion 82b which is set at a predetermined height is projectingly provided.

The second shaft body 82 includes the ring portion 82a. Therefore, the second shaft body 82 is inserted into the second bearing member 83 from an inside end surface side of the second bearing member 83. An outside end surface of the ring portion 82a abuts on the inside end surface of the second bearing member 83 which is protruded from the bottom surface 14c. In the abutting state, an outside end portion of the second shaft body 82 protrudes by a predetermined amount from an outside end surface of the second bearing member 83.

Reference sign 82c of FIG. 8 designates a cutout concave portion. The cutout concave portion 82c is formed at, for example, an outer circumferential edge portion of the ring portion 82a. Reference sign 9p designates a regulation pin. The regulation pin 9p is fixedly provided at a predetermined position in the bore 14b so as to be disposed in the cutout concave portion 82c. The regulation pin 9p protrudes by a predetermined height from the bottom surface 14c. Reference sign 82c1 designates a first abutment surface, and reference sign 82c2 designates a second abutment surface. The regulation pin 9p regulates clockwise rotation of the convex portion 82b by the first abutment surface 82c1 abuts on the regulation pin 9p as shown in the drawing.

Meanwhile, the regulation pin 9p regulates counterclockwise rotation of the convex portion 82b by the second abutment surface 82c2 abutting on the regulation pin 9p. Reference sign 9r designates a dual purpose pin. For example, a pair of dual purpose pins 9r are fixedly provided at predetermined positions of the bore 14b. The dual purpose pin 9r protrudes by a predetermined height from the bottom surface 14c. The dual purpose pin 9r is used as both a positioning pin and a slide auxiliary pin as will be described later.

Figure 9:
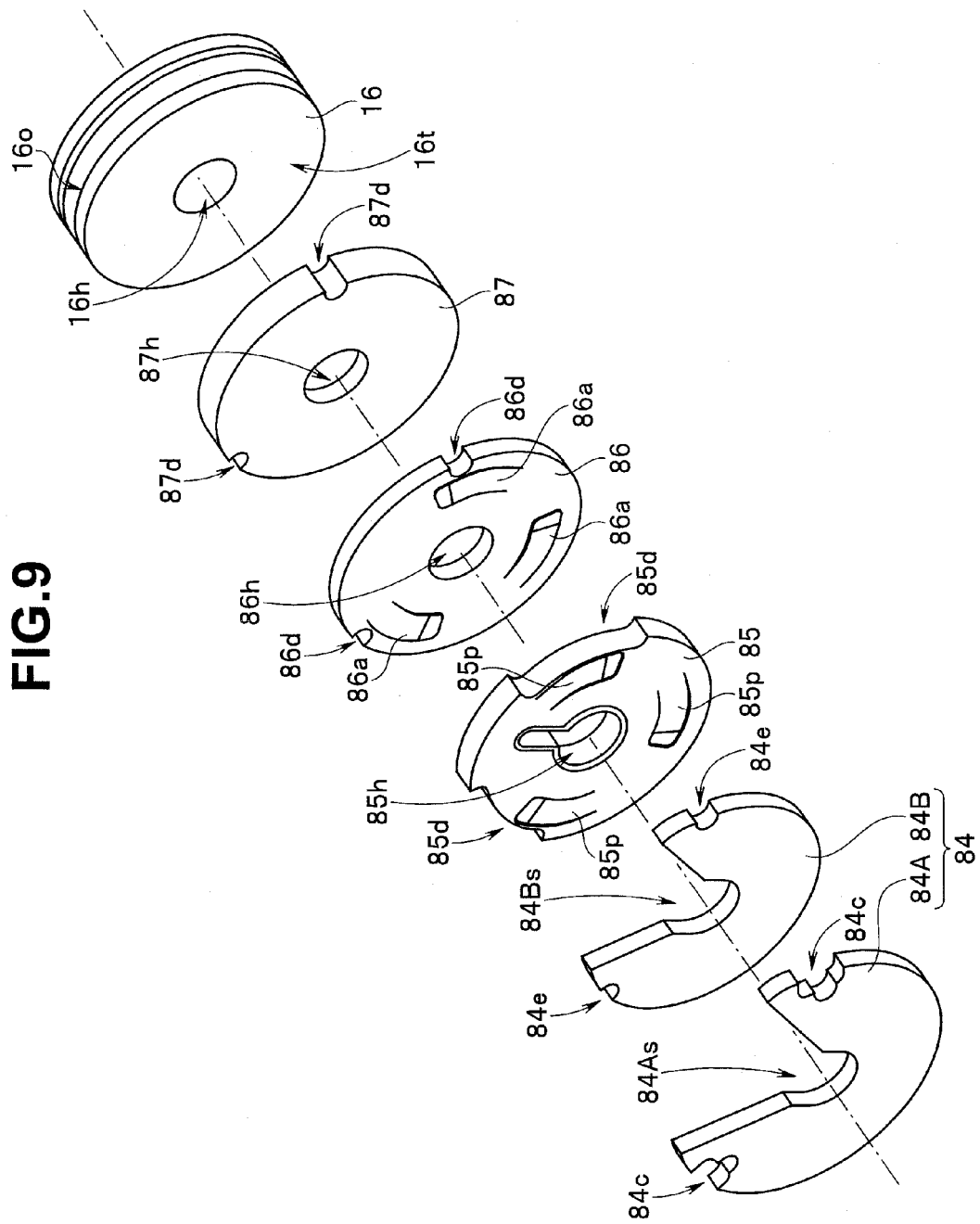
FIG. 9 is a developed perspective view explaining braking elements of the bending portion braking mechanism section incorporated in the bending operation mechanism section.

As shown in FIG. 9, the first braking plate 84A, the second braking plate 84B, the first cam 85, the second cam 86 and the friction member 87 are braking elements. The braking elements are aligned in the sequence of citation described above and fitted in the inside end portion of the first bearing member 15 which is protruded from the bottom surface 14c of the support panel 14 from the blocking cover 37R side.

Figure 10:
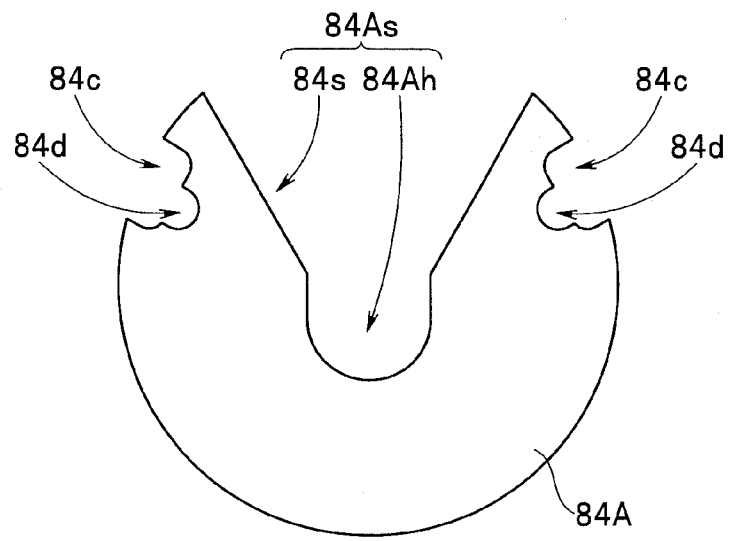
FIG. 10 is a view explaining a first braking plate configuring a first layer of a braking regulating plate.

The first braking plate 84A shown in FIG. 9 and FIG. 10 is, for example, a disk made of a metal such as stainless steel, which has predetermined stiffness with a predetermined thickness dimension. The first braking plate 84A includes, for example, a pair of cutout portions 84c, and one space forming portion 84As. An outside diameter of the first braking plate 84A is set to be smaller than an inside diameter of the bore 14b.

The cutout portion 84c of the first braking plate 84A is provided with a cutout hole 84d. In the cutout holes 84d, a pair of dual purpose pins 9r are disposed. A diameter dimension of the cutout hole 84d is set to be larger than a diameter of the dual purpose pin 9r by a predetermined dimension. According to the configuration, the first braking plate 84A is uniquely disposed in the bore 14b.

Meanwhile, the space forming portion 84As includes a bearing cutout hole 84Ah and a ring portion disposition space 84s. The first bearing member 15 is inserted through the bearing cutout hole 84Ah. The ring portion 82a is disposed in the ring portion disposition space 84s.

Figure 11:
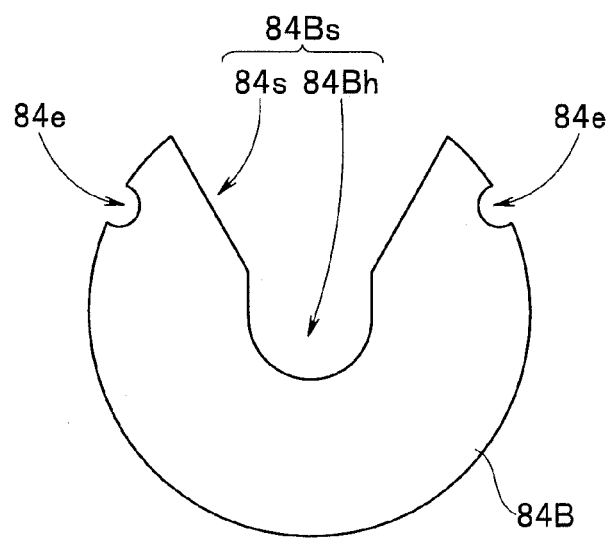
FIG. 11 is a view explaining a second braking plate configuring a second layer of the braking regulating plate.

In contrast with this, the second braking plate 84B shown in FIG. 9 and FIG. 11 is a disk made of a resin with favorable slippage such as polyacetal, for example, with a predetermined thickness dimension. The second braking plate 84B includes, for example, a pair of cutout holes 84e, and one space forming portion 84Bs. An outer shape of the second braking plate 84B is formed to be substantially similar to or smaller than an outer shape of the first braking plate 84A.

The second braking plate 84B is disposed between the first braking plate 84A and the first cam 85. The second braking plate 84B secures slippage of the first braking plate 84A and the first cam 85, and prevents occurrence of a malfunction due to dragging.

In the cutout hole 84e, a pair of dual purpose pins 9r are disposed. The diameter dimension of the cutout hole 84e is set to be larger than the diameter of the dual purpose pin 9r by a predetermined dimension. According to the configuration, the second braking plate 84B is uniquely disposed in the bore 14b.

Meanwhile, the space forming portion 84Bs includes a bearing cutout hole 84Bh and a ring portion disposition space 84s. The first bearing member 15 is inserted through the bearing cutout hole 84Bh. The ring portion 82a is disposed in the ring portion disposition space 84s.

Figure 12:
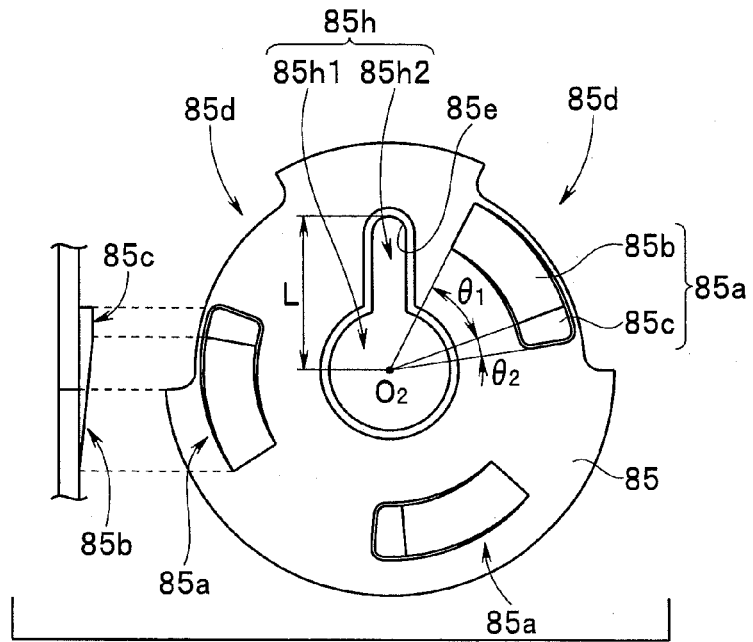
FIG. 12 is a view explaining a first cam.

The first cam 85 shown in FIG. 9 and FIG. 12 is a rotation pressing member configured by a metal disk, in other words, a cam which rotates around an axis of the second bearing member 83.

The first cam 85 is configured by including an oddly shaped hole 85h, for example, three inclined projection portions 85a, and a pair of relief concave portions 85d. The oddly-shaped hole 85h includes a bearing hole 85h1 and a cam hole (groove) 85h2. The first bearing member 15 is inserted through the bearing hole 85h1. The convex portion 82b is disposed movably in the cam hole 85h2.

In the present embodiment, the first cam 85 rotates around an axis with respect to the first bearing member 15 by the convex portion 82b moving in the cam hole 85h2 when the convex portion 82b is moved in the clockwise direction or in the counterclockwise direction with rotation of the second shaft body 82.

The cam hole 85h2 is provided in a predetermined position, and is formed along a radial direction from a center $O_2$. A distance L from the center O2 to a cam hole terminal end 85e of the cam hole 85h2, or a protruded distance from a diameter of the bearing hole 85h1 to the cam hole terminal end 85e is determined in accordance with a rotation amount in the circumferential direction of the convex portion 82b.

For example, three of the inclined projection portions 85a are provided at predetermined positions on the outside side surface of the first cam 85. The three inclined projection portions 85a are formed along the circumferential direction at positions equidistant from the center $O_2$ of the bearing hole 85h1. Each of the inclined projection portions 85a is formed into a mountain shape by including a braking inclined surface (hereinafter, abbreviated as an inclined surface portion) 85b and a braking plane (hereinafter, abbreviated as a flat portion) 85c. The inclined surface portion 85b gradually inclines along a circumferential direction. The flat portion 85c is at a top-most vertex position of the inclined projection portion 85a formed into the mountain shape.

The inclined surface portion 85b of each of the inclined projection portions 85a is formed in the same direction with the same inclination angle (gradient) around the center $O_2$. The flat portion 85c of each of the inclined projection portions 85a is formed at the same height from the outside side surface.

An angle θ1 in the drawing represents a center angle of an effective region of the inclined surface portion 85b, and is, for example, 43 degrees. An angle θ2 in the drawing represents a center angle of an effective region of the flat portion 85c, and is, for example, 10 degrees. In the inclined projection portion 85a, braking which will be described later is performed.

The relief concave portion 85d corresponds to the dual purpose pin 9r, and is formed at the outer circumferential edge portion of the first cam 85. The dual purpose pin 9r is disposed in the relief concave portion 85d. The relief concave portion 85d is formed to prevent the first cam 85 from abutting on the dual purpose pin 9r with movement of the convex portion 82b and hindering rotation.

The first cam 85 including the oddly-shaped hole 85h, the inclined projection portion 85a and the relief concave portion 85d is formed by extrusion by press or the like. However, forming means of the first cam 85 is not limited to forming by extrusion, and may be a method such as cutting machining.

Reference sign 85p of FIG. 9 is an extruded concave portion. The extruded concave portion 85p is a concave portion formed by the inclined projection portion 85a being formed by extrusion.

Figure 13:
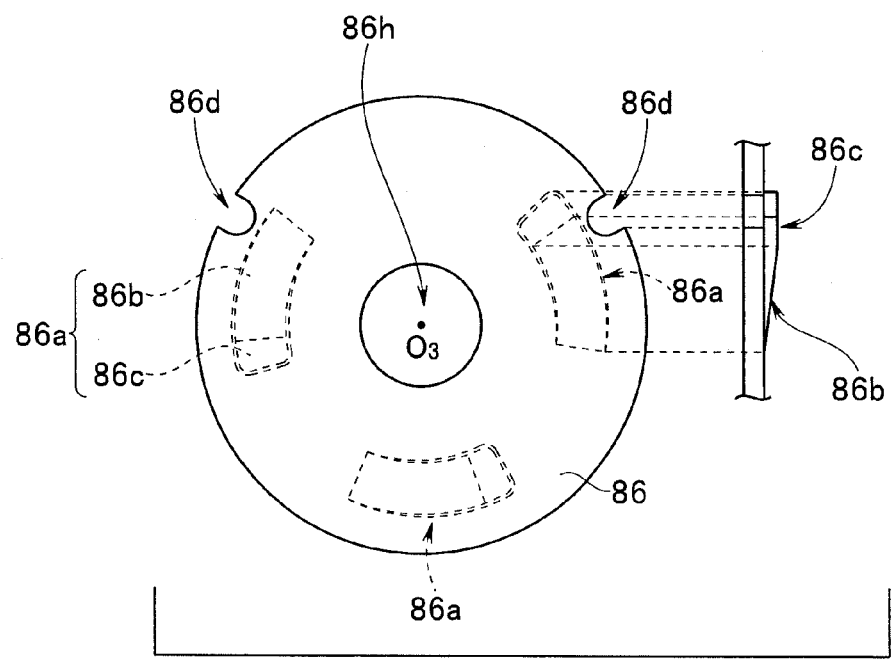
FIG. 13 is a view explaining a second cam.
Figure 14:
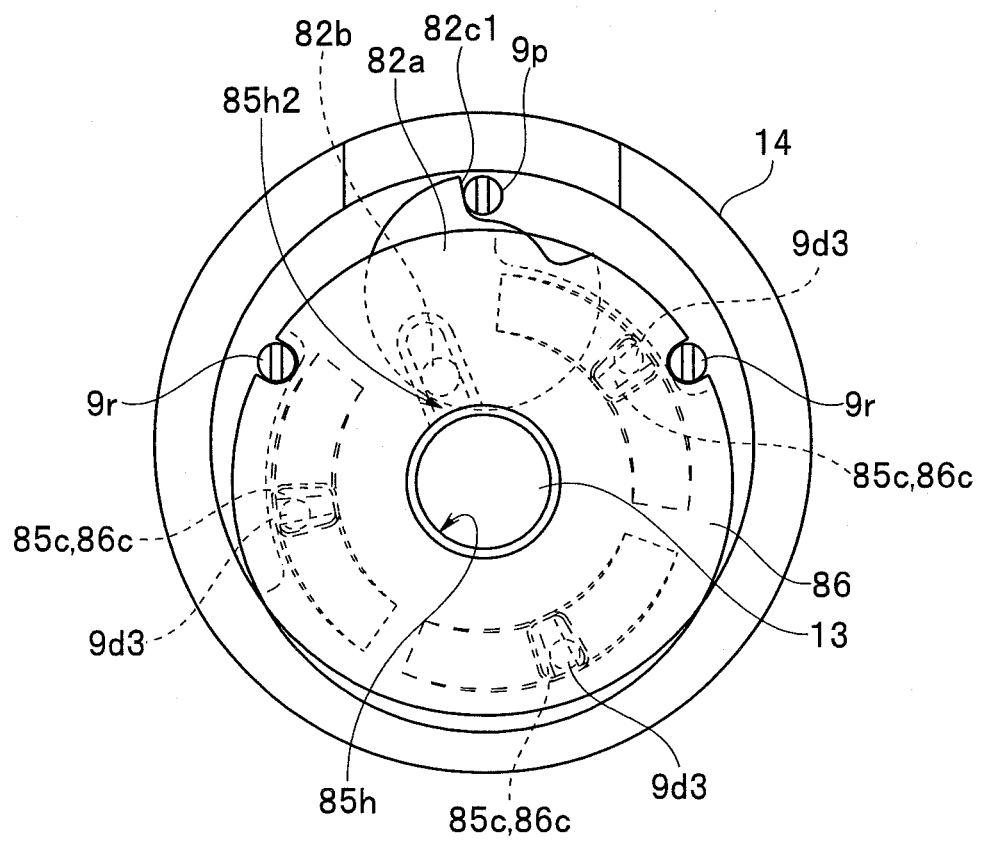
FIG. 14 is a view explaining a relation of disposition positions of a flat portion of the first cam, a flat portion of the second cam, and regulating screws.

The second cam 86 shown in FIG. 9 and FIG. 13 is a slide pressing member configured by a disk of a metal, in other words, a cam which slides in an axial direction of the second bearing member 83. The second cam 86 includes a bearing hole 86h, three inclined projection portions 86a and a pair of cutout holes 86d. The respective inclined projection portions 86a are disposed to be opposed to the respective inclined projection portions 85a.

The first bearing member 15 is inserted through the bearing hole 86h.

For example, three of the inclined projection portions 86a are provided at predetermined positions on an inside side surface of the second cam 86. The three inclined projection portions 86a are formed along a circumferential direction at positions equidistant from a center $O_3$ of the bearing hole 86h similarly to the first cam 85. Each of the inclined projection portions 86a is formed into a mountain shape by including an inclined surface portion 86b and a flat portion 86c. The inclined surface portion 86b is gradually inclined along the circumferential direction.

The inclined surface portion 86b of each of the inclined projection portions 86a is formed in the same orientation at the same inclination angle (gradient) around the center $O_3$. The flat portion 86c of each of the inclined projection portions 86a is formed at the same height from the inside side surface. The flat portion 86c is at a top-most vertex position of the inclined projection portion 86a which is formed into the mountain shape.

In the cutout holes 86d, a pair of dual purpose pins 9r are disposed. A diameter dimension of the cutout hole 86d is set to be larger than the diameter of the dual purpose pin 9r by a predetermined dimension. As a result, the second cam 86 is disposed to be slidable with respect to the first bearing member 15.

FIG. 13 is a view of the second cam 86 seen from the outside side surface where the extruded concave portions are formed instead of seen from the inside side surface where the inclined projection portions 86a are formed. Therefore, in FIG. 13, the inclined projection portions 86a are shown by the broken lines.

The friction member 87 shown in FIG. 9 is, for example, a flat disk made of a resin such as polyether ether ketone (PEEK). The friction member 87 includes a bearing hole 87h and a pair of cutout holes 87d. The first bearing member 15 is inserted through the bearing hole 87h. A pair of dual purpose pins 9r are disposed in the cutout holes 87d. A diameter dimension of the cutout hole 87d is set to be larger than a diameter of the dual purpose pin 9r by a predetermined dimension. As a result, the friction member 87 is disposed to be slidable at the first bearing member 15.

The inside end surface of the pulley 16 is configured as an abutment plane 16t to which an outside end surface of the friction member 87 is pressed.

The first cam 85, the second cam 86 and the friction member 87 which are the braking elements described above are disposed in a gap G of FIG. 5. The gap G is formed between the second braking plate 84B and the abutment plane 16t of the pulley 16 which are disposed in the bore 14b of the support panel 14.

The support panel 14 is an unmovable member as described above, and is placed at a fixed position with respect to the operation section main body 33. Further, the pulley 16 is also configured to be fixedly attached to the first shaft body 13 and not to move in the axial direction of the first shaft body 13. Therefore, the gap G is set at a predetermined value.

Here, disposition positions of the regulating screws 9d1, 9d2 and 9d3, and an operation thereof will be described.

As shown in FIG. 8, the regulating screws 9d1, 9d2 and 9d3 are placed at predetermined positions in the bore 14b of the support panel 14. More specifically, screw distal end faces of the regulating screws 9d1, 9d2 and 9d3 are disposed to be opposed to the flat portions 86c of the inclined projection portions 86a of the second cam 86 which is disposed on the first bearing member 15 without rotating.

The screw distal end faces of the regulating screws 9d1, 9d2 and 9d3 are disposed to configure concaveness with respect to the bottom surface 14c of the bore 14b in an initial state. A distal end of a driver is disposed in a cruciform groove which is provided on a screw head portion, and is advanced, whereby the screw distal end face is gradually protruded from the bottom surface 14c.

The gap G is a distance in a state in which the first braking plate 84A is disposed at a lowermost end of the bore 14b. Accordingly, in the present embodiment, the screw distal end faces of the regulating screws 9d1, 9d2 and 9d3 are gradually protruded from the bottom surface 14c of the bore 14b, whereby the screw distal end faces abut on the first braking plate 84A, and can gradually separate the first braking plate 84A from the bottom surface 14c. More specifically, regulation to narrow the gap G, regulation for increasing the frictional force by moving the outside end surface of the friction member 87 to the abutment plane 16t side of the pulley 16, and increasing the pressing force amount can be performed.

In the present embodiment, the first braking plate 84A and the second braking plate 84B are made separate bodies. However, the first braking plate 84A and the second braking plate 84B may be configured to be integrally fixed. By integral fixation, a gap formed between the first braking plate 84A and the second braking plate 84B is eliminated.

Further, in the present embodiment, the friction member 87 is sandwiched between the pulley 16 and the second cam 86, and is configured to be in sliding contact with both the pulley 16 and the second cam 86. However, a configuration may be adopted, in which the friction member 87 is joined to the inside side surface of the second cam 86 and the friction member 87 is brought into sliding contact with the pulley 16, or a configuration may be adopted, in which the friction member 87 is joined to the abutment plane 16t of the pulley 16, and the inside side surface of the second cam 86 is brought into sliding contact with the friction member 87.

Operations of the bending operation mechanism sections 10A and 10B and the bending portion braking mechanism section 80 will be described.

In a state in which the engage lever 81 is not operated (release position shown by the solid line of FIG. 2), the flat portion 85c of the inclined projection portion 85a of the first cam 85 is in a state slightly lying over the inside side surface of the second cam 86, or over the inclined surface portion 86b. Meanwhile, the flat portion 86c of the inclined projection portion 86a of the second cam 86 is in a state slightly lying over the outside side surface of the first cam 85, or over the inclined surface portion 85b.

In the disposition state, the friction member 87 is not firmly sandwiched by the second cam 86 and the pulley 16. Therefore, when the bending levers 11 and 12 are operated by an operator, the pulley 16 easily and lightly rotates with the operation. As a result, the bending portion 6 is bent with operation of the levers 11 and 12. Even if the pulley 16 and the friction member 87 slightly abut on each other, a frictional force hardly occurs.

When the operator brings the bending portion 6 into a bent state and is to keep the bending state thereof, the operator operates the engage lever 81 and works braking of the bending portion braking mechanism section 80. When the engage lever 81 is rotated to a fixed position shown by the dotted line from the release position shown by the solid line of FIG. 2, the left and the right second shaft bodies 82 integrally rotate.

Thereupon, the convex portion 82b of the ring portion 82a also rotates with rotation of the second shaft body 82. The first abutment surface 82c1 of the cutout concave portion 82c abuts on the regulation pin 9p, whereby a braking completion state is brought about. At this time, the first cam 85 is rotated, and the flat portion 85c of the inclined projection portion 85a of the first cam 85 is disposed on the flat portion 86c of the inclined projection portion 86a of the second cam 86. As a result, the first cam 85 and the second cam 86 are in a relation to push each other strongly.

In the relation, the first cam 85 is inhibited from moving to the outside by the braking plates 84B and 84A. Therefore, only the second cam 86 is moved to the pulley 16 side by the height amounts of the flat portions 85c and 86c. The friction member 87 is disposed between the second cam 86 and the pulley 16. Accordingly, with movement of the second cam 86, the force amount for sandwiching the friction member 87 by the pulley 16 and the second cam 86 increases. Thereupon, the frictional force which occurs between the friction member 87 and the pulley 16 increases, and braking force works on the pulley 16. As a result, the bending state of the bending portion 6 is kept.

However, the operator performs regulation of the braking force when the operator determines that the braking force exerted on the pulley 16 is not sufficient. More specifically, in the state in which the first cam 85 and the second cam 86 strongly push each other, the screw distal end faces of the regulating screws 9d1, 9d2 and 9d3 are gradually protruded from the bottom surface 14c as described above. Thereupon, with protrusion of the screw distal end faces of the regulating screws 9d1, 9d2 and 9d3, the first braking plate 84A and the second braking plate 84B are moved to the outside in the axial direction of the first bearing member 15. As a result, the force amount which sandwiches the friction member 87 by the pulley 16 and the second cam 86 further increases, and the braking force increases. Subsequently, the operator completes regulation when the operator determines that the braking force exerted on the pulley 16 is sufficient.

As above, a metal disk having stiffness is adopted as the first braking plate 84A which is moved by the screw distal end faces abutting thereon with regulation of the protruded amounts of the regulating screws 9d1, 9d2 and 9d3. As a result, the problem of the first braking plate 84A being deformed is solved and application of a load can be efficiently transmitted. In addition, with movement of the first braking plate 84A, the first cam 85, the second cam 86, and the friction member 87 are moved in the axial direction of the first bearing member 15, and the friction member 87 can be uniformly pressed against the abutment plane 16t of the pulley 16.

Further, the braking regulating plate 84 is configured by the first braking plate 84A of a metal having stiffness which configures the first layer, and the second braking plate 84B of a resin with favorable slippage which configures the second layer. The second braking plate 84B is disposed between the first braking plate 84A and the rotatable first cam 85. As a result, with operation of the engage lever 81, the first cam 85 can be smoothly rotated.

Furthermore, the disposition positions of the screw distal end faces of the regulating screws 9d1, 9d2 and 9d3 in the bottom surface 14c of the support panel 14 are set at the positions opposed to the flat portions 86c of the inclined projection portions 86a provided at the second cam 86, which is disposed without rotating.

As a result, when the flat portion 85c of the inclined projection portion 85a of the first cam 85 which is rotated with operation of the engage lever 81 is disposed on the flat portion 86c of the second cam 86, the regulating screw 9d1, the flat portion 85c and the flat portion 86c are disposed in one straight line. Accordingly, the rotational power of the first cam 85 can be converted into the moving power in the axial direction of the second cam 86 without a loss.

Further, the first bearing member 15 is inserted through the first braking plate 84A, the second braking plate 84B, the first cam 85, the second cam 86 and the friction member 87, and the cutout holes 84d, 84e, 86d and 87d in which a pair of dual purpose pins 9r are disposed are formed on the outer circumferential edge portions of the first braking plate 84A, the second braking plate 84B, the second cam 86 and the friction member 87. As a result, the first braking plate 84A, the second braking plate 84B, the second cam 86 and the friction member 87 can be more reliably moved parallel to the axial direction of the first bearing member 15.

Figure 15:
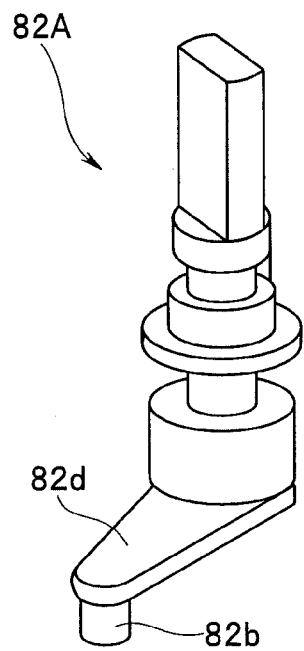
FIG. 15 is a view explaining another configuration of a braking shaft body.

In the embodiment described above, the configuration in which the ring portion 82a including the convex portion 82b is integrally provided on the inside end surface of the second shaft body 82 is adopted. However, the second shaft body 82 is not limited to the configuration, and may have a configuration in which an eccentric plate portion 82d including the convex portion 82b is integrally provided on the inside end surface of a second shaft body 82A, as shown in FIG. 15.

Figure 16:
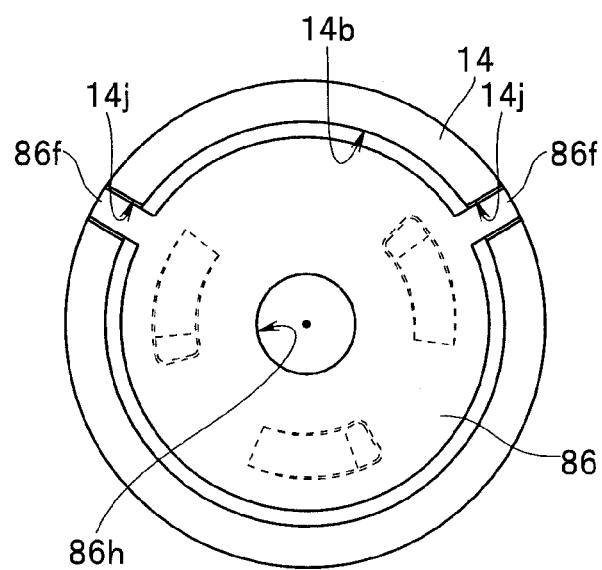
FIG. 16 is a view explaining a relation of the second cam having a pair of projection portions and the support panel having cutout portions where the projection portions are disposed.

Further, in the embodiment described above, a pair of cutout holes 86d are provided at the second cam 86, while the dual purpose pins 9r which are disposed in the cutout holes 86d are provided at the positions corresponding to the cutout holes 86d. However, the configuration which defines the disposition position of the second cam 86 is not limited to the relation of the cutout holes 86d and the dual purpose pins 9r. For example, as shown in FIG. 16, a configuration may be adopted, in which a pair of projection portions 86f are provided at the second cam 86, while cutout portions 14j are provided at the support panel 14. In the cutout portions 14j, the projection portions 86f are respectively engaged and disposed.

Furthermore, in the bending operation apparatus 10 provided in the operation section 3, essential parts not illustrated of the vertical bending operation mechanism section 10A and the lateral bending operation mechanism section 10B are coated with grease with predetermined viscosity to enhance slidability, for the purpose of smoothly operating the vertical lever 11, the lateral lever 12 and the engage lever 81.

However, the grease which is coated for the purpose of enhancing slidability enters a gap between the pulley 16 and the friction member 87, whereby the braking force is reduced, and a problem is likely to occur in keeping the bending state of the bending portion 6.

Figure 17:
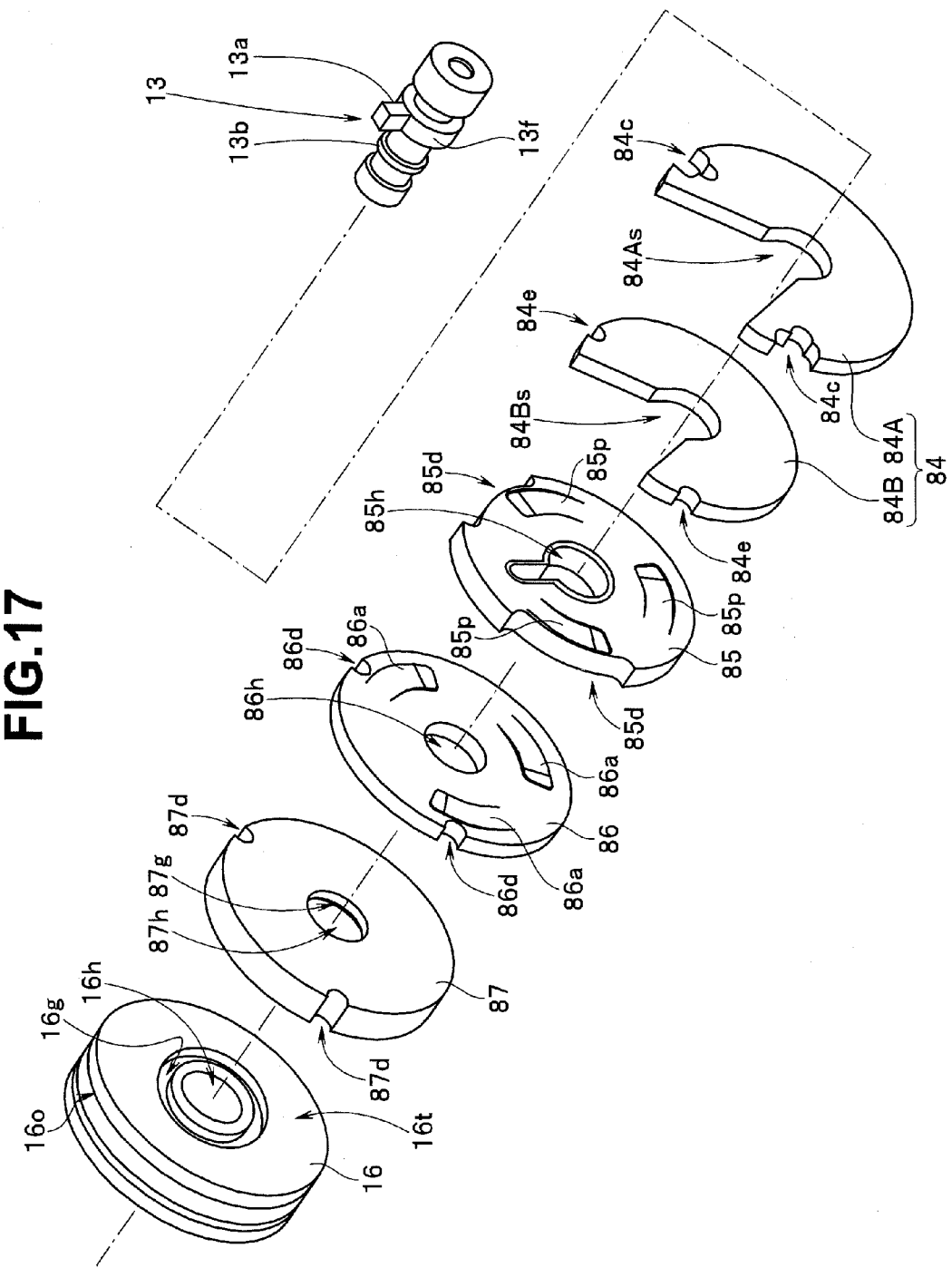
FIG. 17 is a view explaining another configuration of the bending operation mechanism section.

Therefore, as shown in FIG. 17, a circumferential convex portion 13b in a convex shape jutting out with respect to the outer circumferential direction from an intermediate portion bottom surface in a groove 13g which is at a predetermined position of the first shaft body 13 is provided, while a ring groove 16g in a ring shape is provided at a predetermined position on the abutment plane 16t side of the pulley 16, and a release groove 87g is provided on a plane opposed to the abutment plane 16t of the friction member 87.

Figure 18:
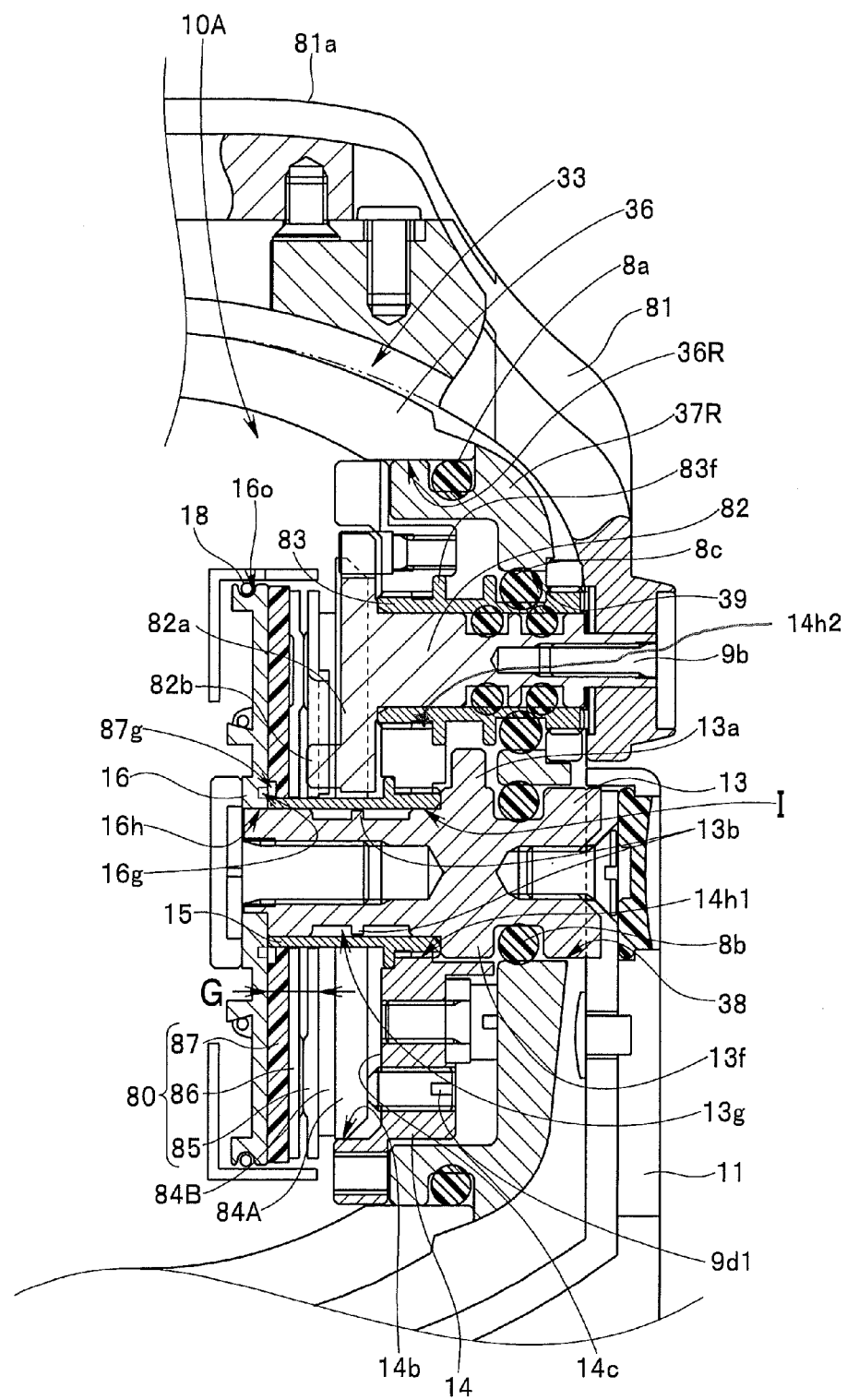
FIG. 18 is a view explaining an operation of the bending operation mechanism section.

A fitting part I of the first bearing member 15 and the first shaft body 13 shown in FIG. 18 is coated with grease. The circumferential convex portion 13b protrudes in the groove 13g which is located at the friction member 87 side from the fitting portion I. The release groove 87g forms a space at a distal end face side of the first bearing member 15, and an opening of the ring groove 16g is located at a space which the release groove 87g forms.

According to the configuration, when the grease with which the fitting portion I is coated enters one space of the groove 13g, the entry into the other spaces is shut off by the circumferential convex portion 13b. As a result, entry of the grease to between the pulley 16 and the friction member 87 is shut off.

If the grease passes the circumferential convex portion 13b and enters the other spaces, entry of the grease to between the pulley 16 and the friction member 87 is shut off by the release groove 87g and the ring groove 16g. More specifically, when the grease which enters the other spaces passes the fitting portion of the first bearing member 15 and the first shaft body 13 and reaches the distal end face side of the first bearing member 15, the grease stays in the space formed by the release groove 87g and the space formed by the ring groove 16g, and entry to between the pulley 16 and the friction member 87 is shut off.

As above, the circumferential convex portion 13b, the ring groove 16g and the release groove 87g are provided, whereby the grease with which the fitting portion I is coated can be reliably prevented from entering a gap between the pulley 16 and the friction member 87.

Incidentally, in the engage lever 81, a problem such as breakage and bend is likely to occur as a result that the engage lever 81 is operated with a force which is more than necessary. Therefore, the engage lever in which occurrence of a problem is prevented even if the engage lever is operated with the force which is more than necessary is desired.

Figure 19A:
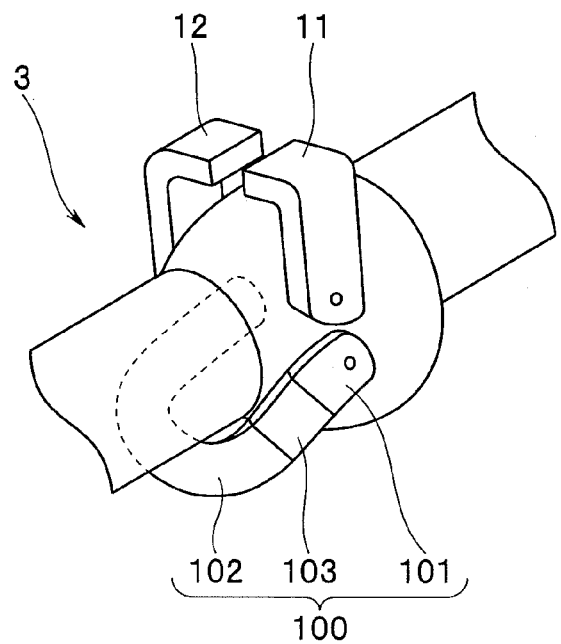
FIG. 19A is a view explaining another configuration of the bending state keeping lever.

As shown in FIG. 19A, an engage lever 100 of the present embodiment is configured by including a rotation fixing section 101, a finger rest portion 102, and an elastic deformation portion 103. The rotation fixing sections 101 are made of a rigid resin, and configure both end portions of the engage lever 100. The finger rest portion 102 is made of a rigid resin similarly to the rotation fixing section 101. The finger rest portion 102 is provided in an intermediate portion of the engage lever 100. The elastic deformation portion 103 is provided at least between the finger rest portion 102 and one of the rotation fixing sections 101. The elastic deformation portion 103 is made of elastomer such as a rubber including a predetermined elastic force, or made of a metal such as a spring.

In the drawings, the elastic deformation portions 103 are included at both sides with the finger rest portion 102 therebetween.

Figure 19B:
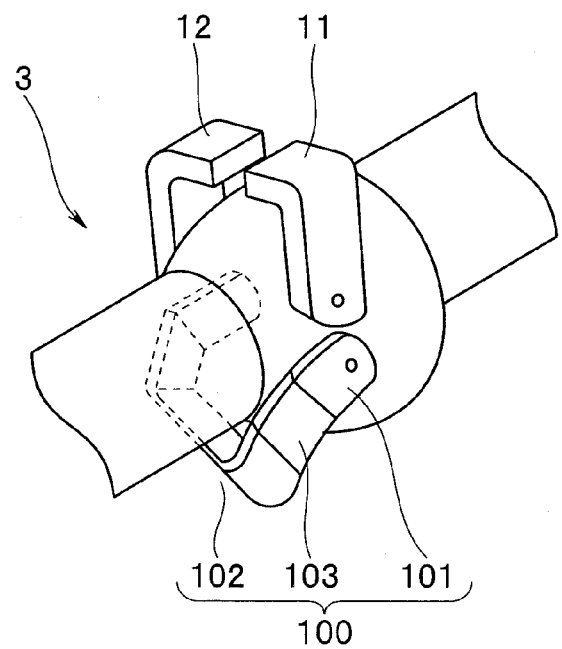
FIG. 19B is a view explaining an operation of the bending state keeping lever shown in FIG. 19A.

According to the configuration, when the elastic deformation portions 103 are operated with a force amount more than the predetermined force amount, the elastic deformation portions 103 are deformed as shown in FIG. 19B and are changed into a bent state.

The elastic deformation portions 103 include such elasticity that the elastic deformation portions 103 are restored into the original shapes by fingers being taken off from the engage lever 100.

Figure 20:
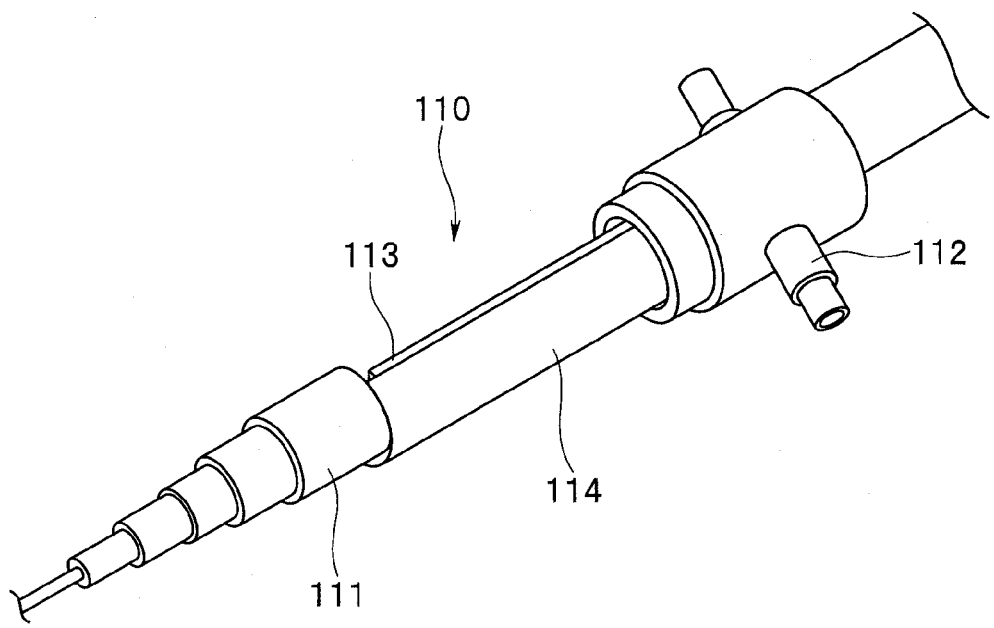
FIGS. 20 to 22 are views explaining a configuration of a light guide connector which reliably and electrically continues two corrugated tube pipe sleeves included in the light guide connector according to another configuration example of the light guide connector.

Incidentally, in the light guide connectors of endoscopes, some light guide connectors are each of a type having two corrugated tube pipe sleeves 111 and 112 in a light guide connector 110 as shown in FIG. 20. Conventionally, in the case of the connector having the two corrugated tube pipe sleeves 111 and 112, conductivity have been achieved with an internal metal body. However, the number of connection components is large, and the connection portions are bonded, whereby degradation of the conductive performance is feared.

In the present embodiment, a conductive frame member 113 which extends from the first corrugated tube pipe sleeve 111 to the second corrugated tube pipe sleeve 112 is provided in the light guide connector 110, and a conductive metal body 114 is integrally provided at the frame member 113. The conductive metal body 114 is a thin plate of, for example, copper which is elastically deformable.

Figure 21:
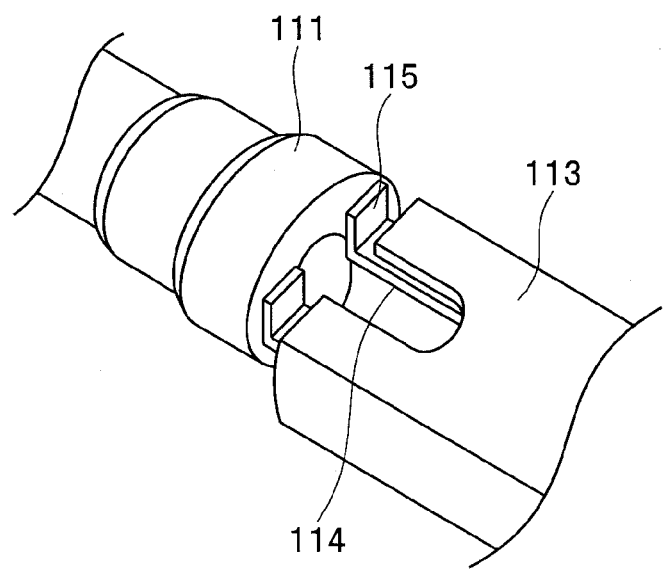

The respective corrugated tube pipe sleeves 111 and 112 are respectively connected to the frame member 113. As shown in FIG. 21, an elastic contact point 115 which is provided at the frame member 113 and is configured by the conductive metal body 114 is electrically in contact with an end surface of the first corrugated tube pipe sleeve 111. Further, an elastic contact point not illustrated which is provided at the frame member 113 and is configured by the conductive metal body 114 is electrically in contact with an end surface not illustrated of the second corrugated tube pipe sleeve 112.

According to the configuration, even with the configuration which bonds and fixes the corrugated tube pipe sleeves to the frame member, the first corrugated tube pipe sleeve 111 and the elastic contact point 115 of the conductive metal body 114 provided at the frame member 113 are electrically continued reliably, and the second corrugated tube pipe sleeve 112 and the elastic contact point 115 of the conductive metal body 114 are electrically continued reliably. As a result, occurrence of EMC noise is prevented.

Figure 22:
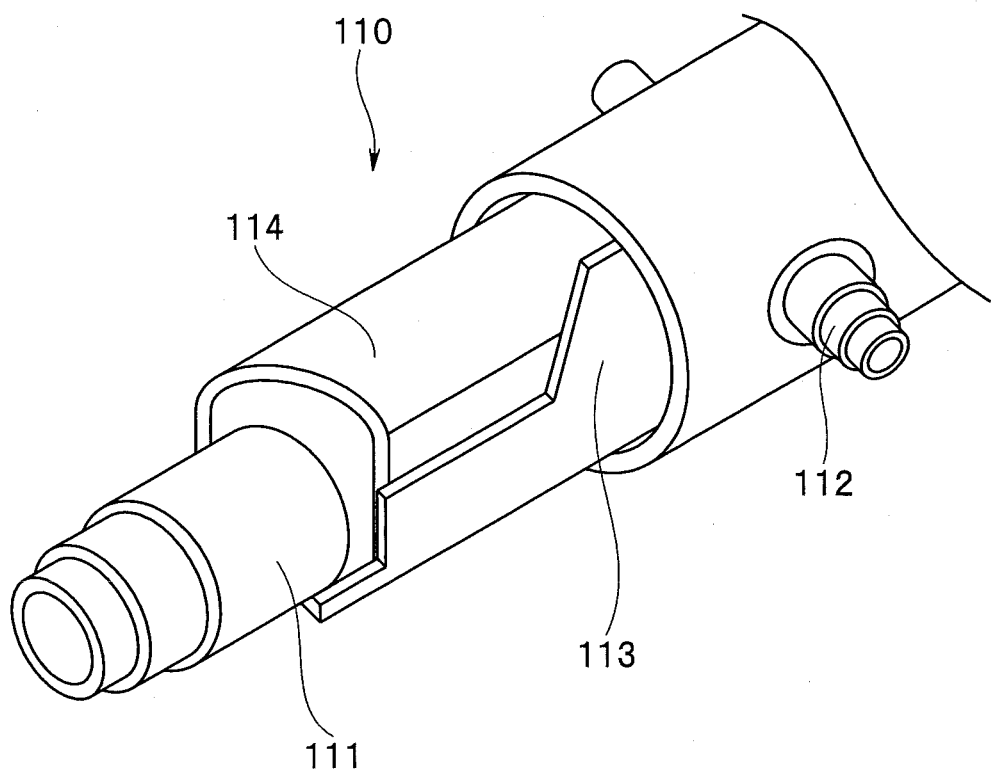

As shown in FIG. 22, an image pickup signal cable may be inserted through an inside of a space configured by the frame member 113 and the conductive metal body 114. In the configuration, the frame member 113 and the conductive metal body 114 are also used as a shield case.

Incidentally, it has been conventionally desired to convert an analogue signal which is transmitted from a CCD contained in the distal end portion of an insertion portion into a digital signal without attenuating the analog signal as much as possible.

Figure 23:
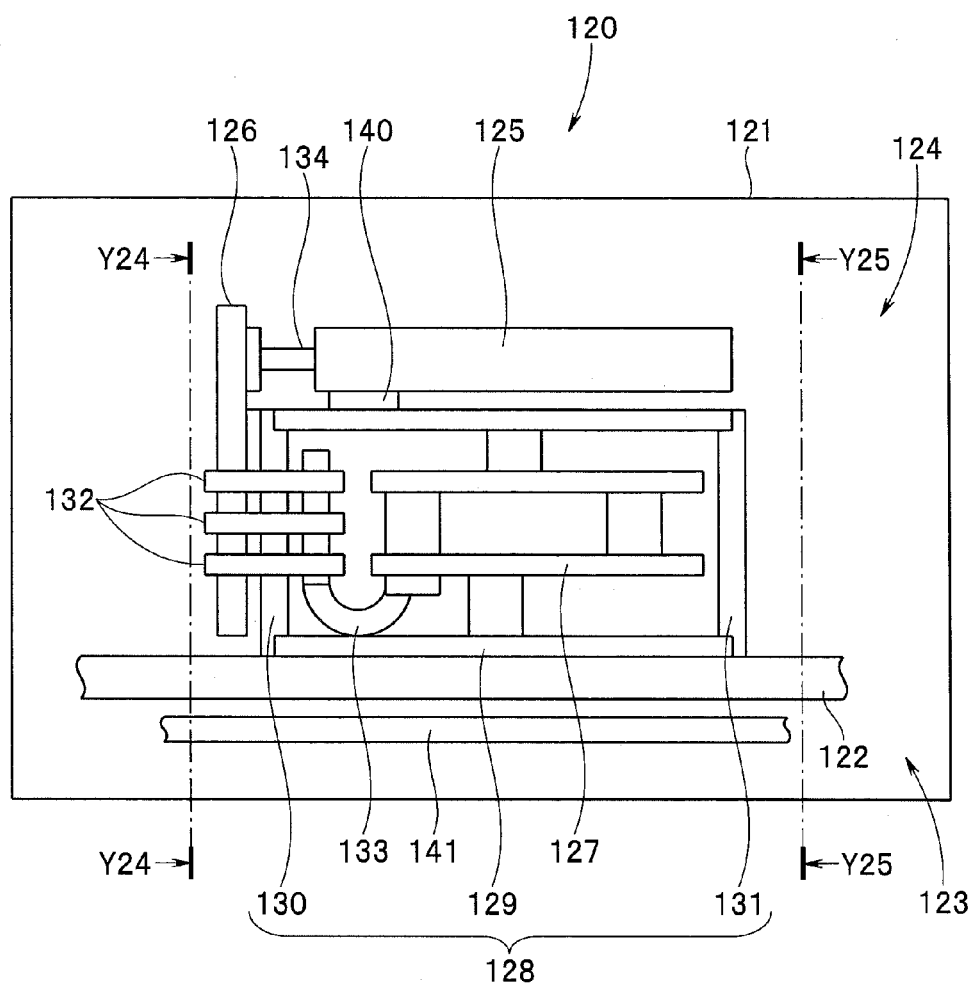
FIGS. 23 to 25 are schematic views according to another configuration example of the light guide connector, and explaining a configuration in which an AD conversion circuit is provided in a connector.
Figure 24:
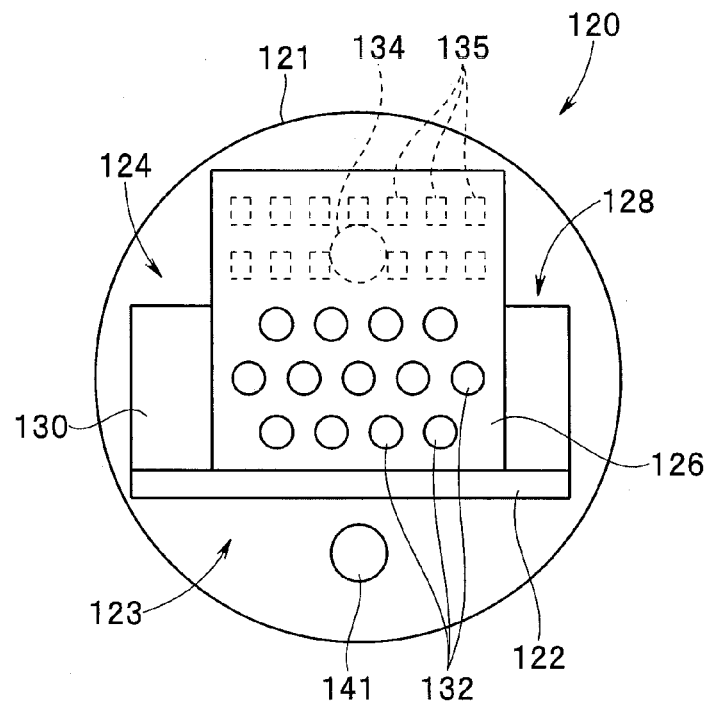
Figure 25:
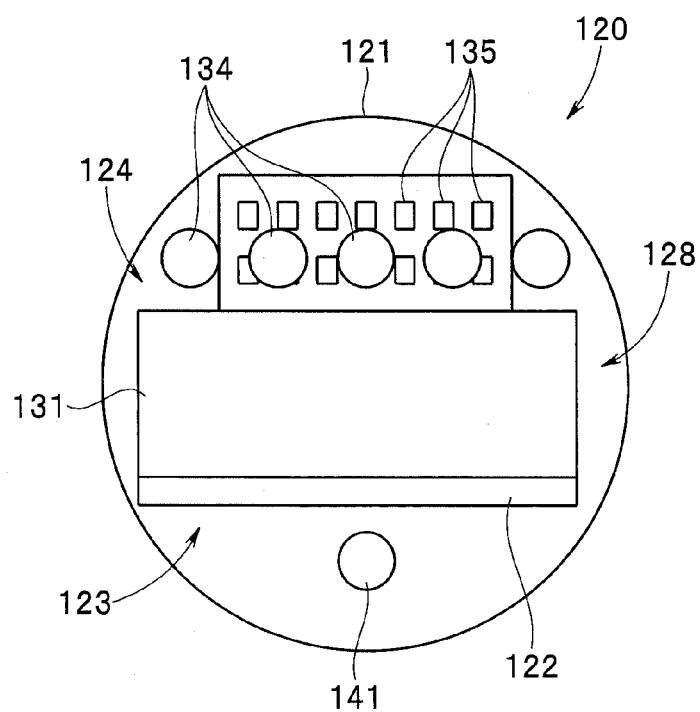

As shown in FIG. 23 to FIG. 25, in a light guide connector 120 of the present embodiment, an internal space of a case body 121 is divided into a light guide housing space 123 and an A/D converting space 124 by a frame member 122.

In the light guide housing space 123, a light guide bundle 141 is housed with consideration given to an allowance length for a time of repair.

In the A/D converting space 124, an image pickup signal cable 125, a cable connecting board 126 and an A/D conversion circuit board 127 are housed. The A/D conversion circuit board 127 is placed in a frame body 128 configuring an airtight space for the purpose of being given autoclave resistance. The frame body 128 is configured by including a rectangular pipe member 129, a front surface member 130 and a back surface member 131. The rectangular pipe member 129 is made of a metal and has a tetragonal sectional shape. The front surface member 130 and the back surface member 131 are plate members made of a metal.

The front surface member 130 is provided with a plurality of connection pins 132. The respective connection pins 132 are disposed in through-holes which are formed in the front surface member 130 respectively. The connection pin 132 is air-tightly joined by, for example, soldering so that a gap does not occur between the connection pin and the through-hole.

One end of the connection pin 132 and a connection portion of the A/D conversion circuit board 127 are connected via a connection line 133. The other end of the connection pin 132 is directly connected to a connection portion provided at the cable connecting board 126.

A plurality of signal lines 134 which are inserted into the image pickup signal cable 125 are respectively connected to predetermined connecting portion 135.

The rectangular pipe member 129 and the front surface member 130 are air-tightly joined by, for example, soldering, and the rectangular pipe member 129 and the back surface member 131 are air-tightly joined by, for example, soldering.

As a result, the A/D conversion circuit board 127 is disposed in an air-tight space.

The light guide connector 120 is configured as described above, whereby the light guide bundle 141 can be housed without consideration given to the disposition positions of the other contained components.

Further, it is not necessary to consider the disposition positions of the other contained components, and therefore, the cable connecting board 126 which is formed with the maximum area can be disposed in the A/D converting space 124. As a result, a connecting operation of the connection pins 132 and the connecting operation of the signal lines 134 can be efficiently performed.

In addition, the image pickup signal cable 125 and the signal line 134 can be placed in a space configured by the rectangular pipe member 129 and the case body 121.

Digital image pickup signals can be outputted from the light guide connector 120.

Reference sign 140 designates a cable fixing member. In the present embodiment, the image pickup signal cable 125 is fixedly provided in a top surface in the drawing of the rectangular pipe member 129 by the cable fixing member 140.

Further, in the embodiment described above, the cable connecting board 126 is provided to be orthogonal to a longitudinal axis direction of the case body 121. However, the disposition of the cable connecting board 126 in the case body 121 is not limited to the direction orthogonal to the longitudinal axis direction. For example, as shown in FIG. 26 and FIG. 27, the configuration in which the cable connecting board 126 is disposed parallel with the longitudinal axis direction of the case body in the case body 121 may be adopted.

Figure 26:
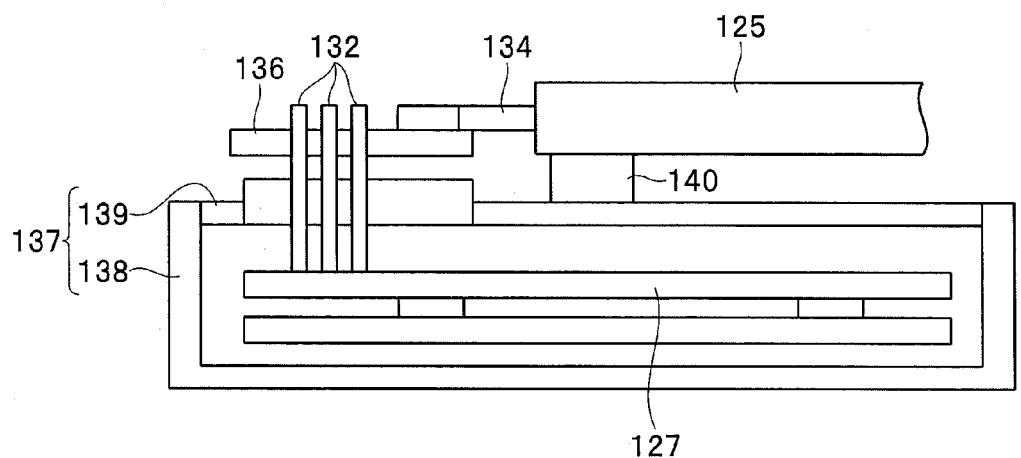
FIG. 26 is a front view explaining a configuration of the light guide connector in which a cable connecting board disposed in an A/D converting space is disposed parallel to a longitudinal axis direction of a case body.
Figure 27:
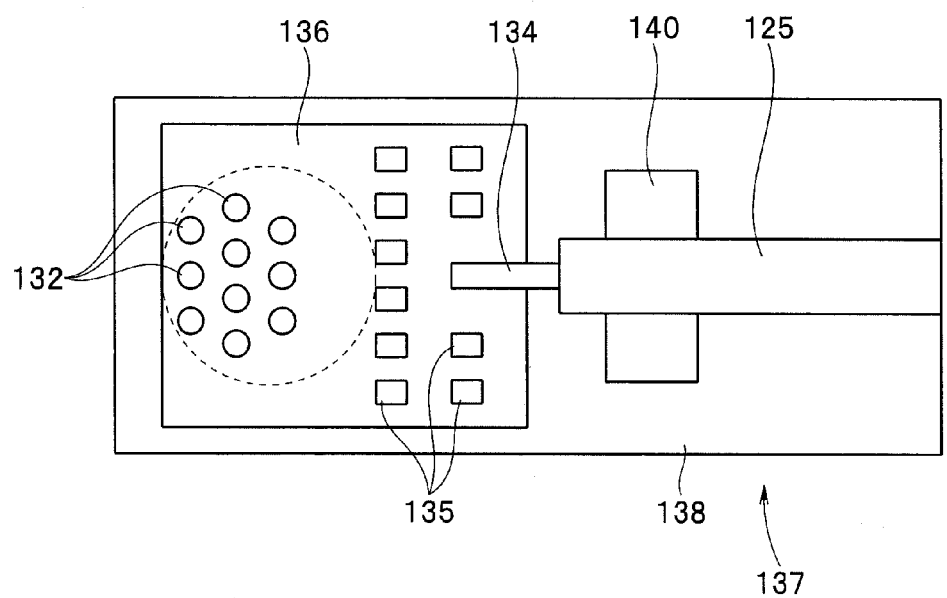
FIG. 27 is a top view of the light guide connector of FIG. 26.

As shown in FIG. 26 and FIG. 27, in the present embodiment, a cable connecting board 136 which is housed in the A/D converting space 124 is disposed parallel to the longitudinal axis direction of the case body not illustrated.

In the A/D converting space 124, the image pickup signal cable 125, the cable connecting board 136, and the A/D conversion circuit board 127 are housed. The A/D conversion circuit board 127 is placed in a frame body 137 which configures an air-tight space for the purpose of being given autoclave resistance. The frame body 137 is configured by including a box-shaped member 138 and a lid member 139. The box-shaped member 138 is made of a metal with a sectional shape being in a rectangular parallelepiped shape. The lid member 139 is a plate member of a metal.

The lid member 139 is provided with a plurality of connection pins 132. The respective connection pins 132 are disposed in through-holes which are formed in the lid member 139 respectively. The connection pins and the through-holes are air-tightly joined by, for example, soldering so that a gap does not occur between the connection pins 132 and the through-holes. Further, the image pickup signal cable 125 is fixedly provided at a top surface in the drawing of the lid member 139 via the cable fixing member 140.

One end of the connection pin 132 is directly connected to a connection portion of the A/D conversion circuit board 127. The other end of the connection pin 132 is directly connected to a connection portion provided at the cable connecting board 136.

A plurality of signal lines 134 inserted into the image pickup signal cable 125 are respectively connected to the predetermined connection portions 135.

The box-shaped member 138 and the lid member 139 are air-tightly joined by, for example, soldering. As a result, the A/D conversion circuit board 127 is disposed in an airtight space.

According to the configuration, a space on the frame body 137 is effectively used, and a space in the light guide connector can be effectively used. The other operation and effect are the same as in the embodiment shown in FIG. 23 to FIG. 25 described above.

Figure 28:
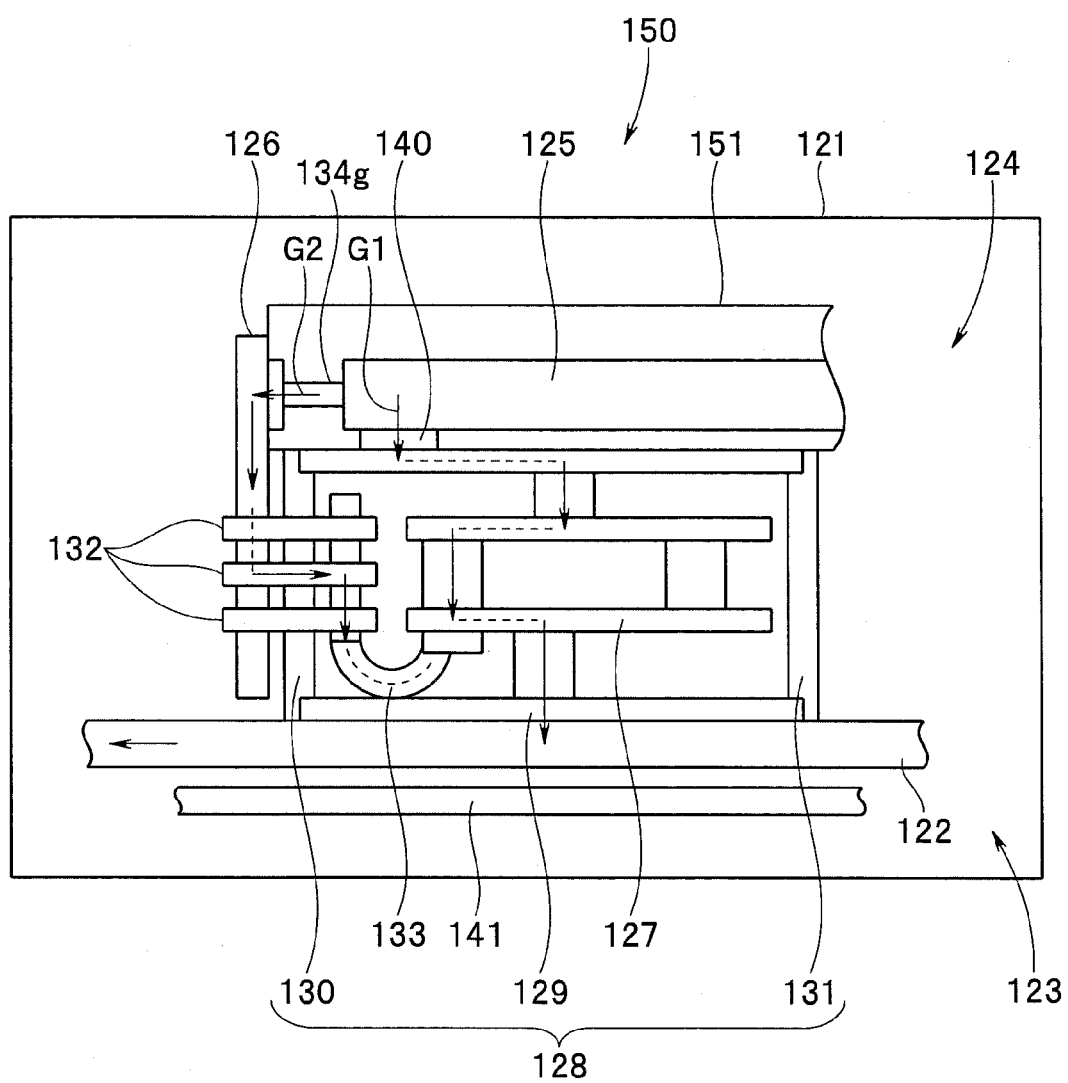
FIG. 28 is a view explaining a configuration example of the light guide connector which improves a shield performance.

In a light guide connector 150 shown in FIG. 28, a first ground route G1 and a second ground route G2 are provided. The first ground route G1 is provided for the purpose of further shielding the covered image pickup signal cable. The second ground route G2 is provided for the purpose of performing shield for a soldered signal line.

In order to provide the ground routes G1 and G2, the image pickup signal cable 125 which is inserted in the case body 121 is covered with a shield case 151. Further, an external conductor of the image pickup signal cable 125 and the shield case 151 are electrically connected via the cable fixing member 140. In addition, the shield case 151 is electrically connected to a top surface in the drawing of the rectangular pipe member 129 which configures the frame body 128. Further, the A/D conversion circuit board 127 which is placed in the frame body 128 is held by a spacer 152 of a metal having conductivity. As a result, the first ground route G1 is provided.

Meanwhile, a ground line 134g in the image pickup signal cable 125 is connected to a ground connection pin 132g via the cable connecting board 126. The ground connection pin 132g and the ground of the A/D conversion circuit board 127 are connected with a ground connection line 133g. As a result the second ground route G2 is provided. The frame member 122 is connected to a general ground (not illustrated).

According to the configuration, shield of the covered image pickup signal cable, and shield for the signal line which is soldered can be reliably performed.

Incidentally, in the image pickup connector of an endoscope, conductivity is achieved by the corrugated tube pipe sleeve and the metal body in the connector. However, adhesion is used for the connection portion, whereby there arises the fear of reducing the conductive performance. Further, in the configuration in which a board is provided in the connector, operations at the time of the board being extracted from the inside of the connector, and at the time of the board being connected to the inside of the connector are complicated. Therefore, a conduction structure which is excellent in operability and provides a reliable conductive performance is desired.

Figure 29:
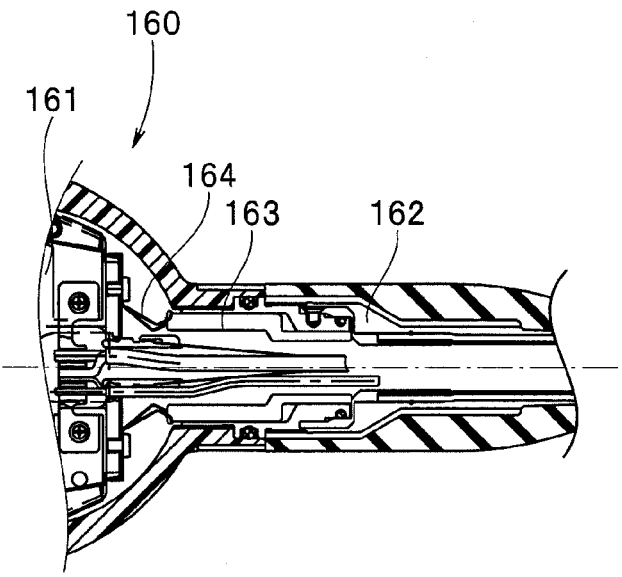
FIG. 29 is a view explaining a configuration example of an image pickup connector.

As shown in FIG. 29, in an image pickup connector 160 of the present embodiment, electric continuity of a board 161 in the connector and a corrugated tube pipe sleeve 162 is achieved by a first conductive member 163 and a second conductive member 164.

Figure 30:
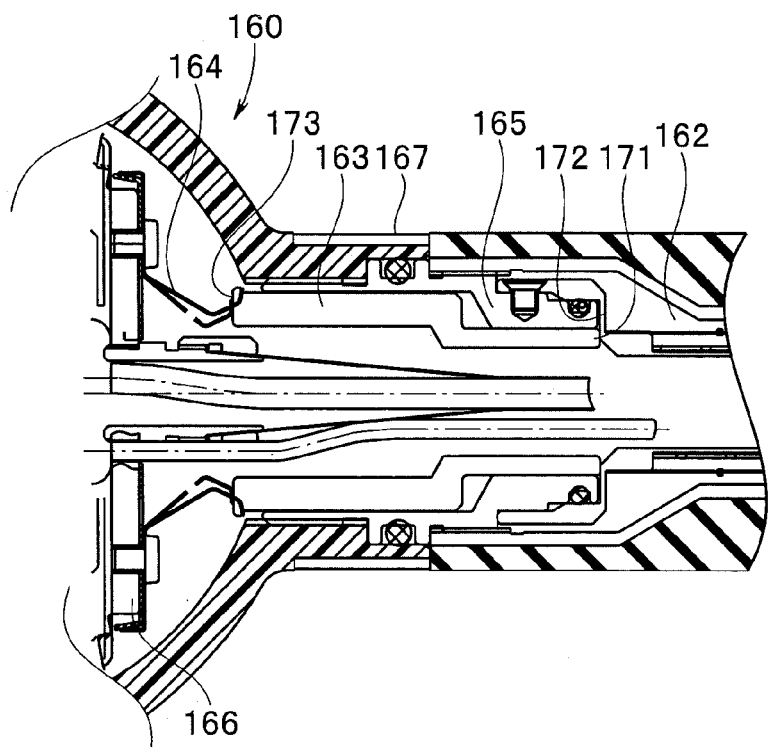
FIG. 30 is a an enlarged view of a main part of FIG. 29 and is a view explaining a first conductive member and a second conductive member which electrically continue a board and the corrugated tube pipe sleeve.

As shown in FIG. 30, the first conductive member 163 is slidably disposed in a connector connection member 165. A pipe sleeve side end surface 171 of the first conductive member 163 is configured to abut on a connector side end surface 172 of the corrugated tube pipe sleeve 162.

The second conductive member 164 is a finger member which is formed into a predetermined bent shape by a plate spring member having a predetermined elastic force. One end of the second conductive member 164 is fixed by, for example, screwing to a board ground 166. The other end of the second conductive member 164 abuts on and is disposed at an end surface 173 of the first conductive member 163. In the abutment state, the first conductive member 163 is moved to a pipe sleeve side by the elastic force of the second conductive member 164. The pipe sleeve side end surface 171 of the first conductive member 163 abuts and is disposed on the connector side end surface 172 of the corrugated tube pipe sleeve 162 by an elastic force.

According to the configuration, electric continuity of the board 161 and the corrugated tube pipe sleeve 162 can be reliably and easily performed with the second conductive member 164 one end of which is fixed to the board ground 166 of the board 161, and the first conductive member 163 which is disposed by abutting on the corrugated tube pipe sleeve 162 by the elastic force of the second conductive member 164.

Reference sign 167 designates a nameplate. In the present invention, the nameplate 167 is formed by a nonconductive member. The nameplate 167 is configured by a nonconductive member, whereby the problem which occurs by static electricity which occurs in the air flowing in the nameplate 167 is eliminated. When the nameplate 167 is made of a metal, nonconductive transparent coating is applied to the surface of the nameplate 167, whereby the above described problem is eliminated.

Incidentally, in animal laboratories, a number of forceps have been conventionally used. Therefore, an instrument in which a plurality of forceps are disposed on an instrument table by being organized has been desired by users.

Figure 31:
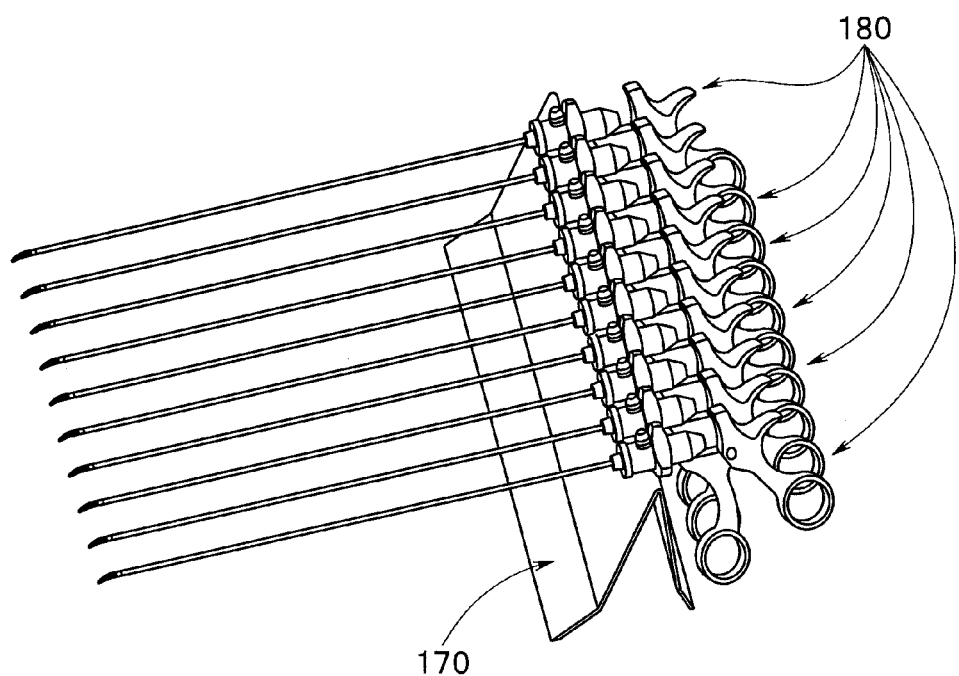
FIG. 31 is a view showing a forceps table and a plurality of forceps which are disposed on the forceps table.
Figure 32:
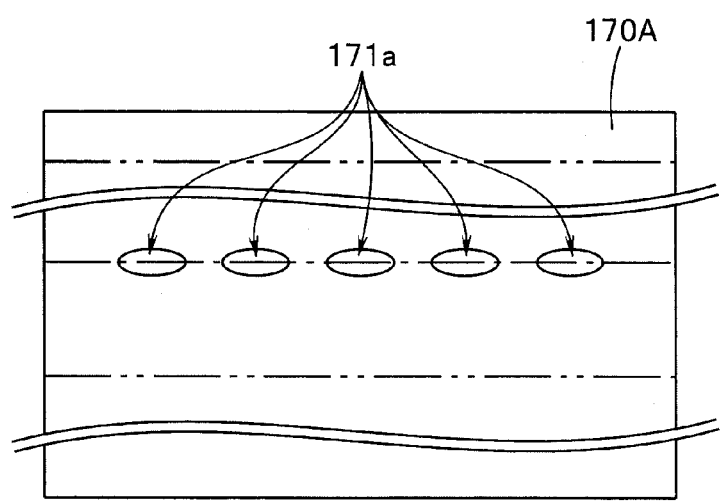
FIG. 32 is a developed view of the forceps table.

Reference sign 170 of FIG. 31 designates a forceps table, and on the forceps table 170, a plurality of forceps 180 are aligned and disposed. The forceps table 170 is a flat plate member 170A of stainless steel, and a plurality of elliptic holes 171a which configure a support portion 171 are formed as shown in, for example, FIG. 32.

Figure 33:
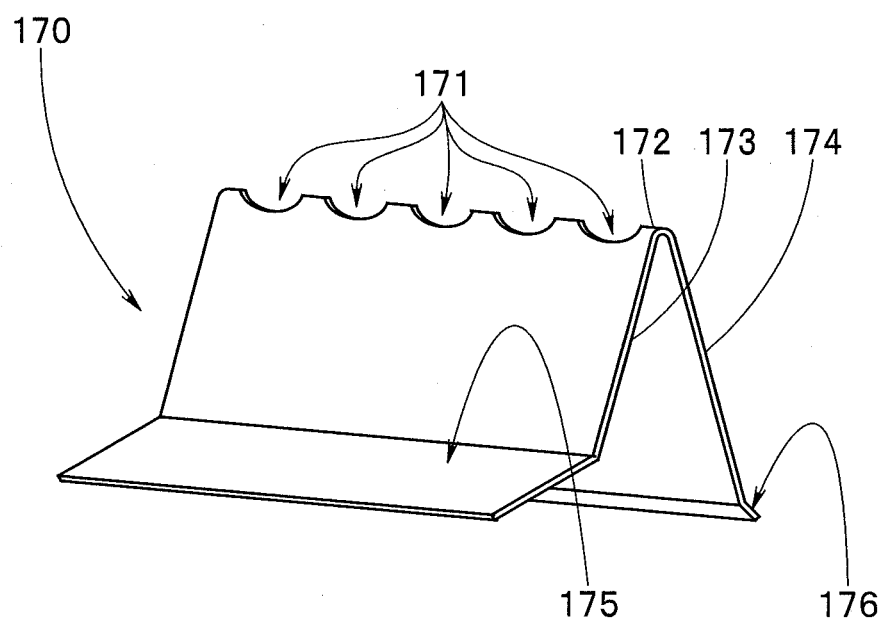
FIG. 33 is a view explaining a configuration of the forceps table.

As shown in FIG. 33, the forceps table 170 is configured into a predetermined shape by the flat plate member 170A being folded. The forceps table 170 includes a folded portion 172 having a plurality of support portions 171, a first support portion 173 and a second support portion 174. The first support portion 173 and the second support portion 174 are provided with the folded portion 172 therebetween. An angle formed by the first support portion 173 and the second support portion 174 is set at, for example, 30 degrees. The folded portion 172 is a ridge line of the first support portion 173 and the second support portion 174.

The first support portion 173 is provided with a first bent portion 175, and the second support portion 174 is provided with a second bent portion 176. The first support portion 173 is provided with the first bent portion 175, and the second support portion 174 is provided with the second bent portion 176, whereby the forceps table 170 is stably placed on the instrument table.

As above, the forceps table 170 having a plurality of support portions 171 is configured, whereby a number of forceps can be disposed on the instrument table in alignment, in an animal laboratory.

The present invention is not limited only to the embodiment described above, and can be carried out by being variously modified within a range without departing from the gist of the invention.

What is claimed is:

1. An endoscope including an insertion portion having a bendable bending portion, and an operation section connectively provided at a proximal end side of the insertion portion, and including, in the operation section, a bending operation apparatus which is operated when the bending portion is caused to perform a bending operation, wherein the bending operation apparatus includes a bending operation mechanism section and a bending portion braking mechanism section, the bending operation mechanism section comprises a bending lever which is rotatably disposed at an operation section main body of the operation section, and is rotated when the bending portion is caused to perform the bending operation, a first bearing member that pivotally and rotatably supports a bending operation shaft body which has the bending lever integrally fixed to one end of the bending operation shaft body, and transmits a rotation force of the bending lever, and is fixed to a support panel integral with the operation section main body, and a cylindrical member that is fixedly provided integrally at an other end of the bending operation shaft body, is rotated with a rotational operation of the bending lever, and pulls and loosens an operation wire which is disposed in an outer circumferential groove, and the bending portion braking mechanism section comprises a bending state keeping lever that is rotatably disposed at the operation section main body of the operation section, and is operated when a bending state of the bending portion which is bent is kept, a braking shaft body that has the bending state keeping lever integrally fixed to one end, and transmits a rotation force of the bending state keeping lever, a second bearing member that pivotally and rotatably supports the braking shaft body, and is fixed to the support panel, a rotation pressing member that includes a bearing hole in which the first bearing member is rotatably disposed and a cam hole in which a convex portion of the braking shaft body is movably disposed, rotates around an axis of the first bearing member with a rotational operation of the braking shaft body, and has a plurality of inclined projection portions, a slide pressing member that is disposed slidably in an axial direction of the first bearing member, and has a plurality of inclined projection portions opposed to the inclined projection portions of the rotation pressing member, a friction member that is slidable in the axial direction of the first bearing member, is disposed between the slide pressing member and the cylindrical member, and is capable of abutting on the cylindrical member, a regulation member that is disposed between the rotation pressing member and the support panel, is slidable in the axial direction of the first bearing member, and is capable of regulating a gap in which the rotation pressing member, the slide pressing member and the friction member are disposed, the regulation member including at least a first braking plate configuring a first layer and a second braking plate configuring a second layer, the first braking plate being made of a metal and configured to transmit application of a load without being deformed, and the second braking plate being made of a resin and configured to secure slippage and prevent occurrence of dragging, and a plurality of positioning members that are disposed at the support panel by screwing, separate the regulation member from the support panel by changing an abutment state on the regulation member, and regulate a braking force of the friction member to the cylindrical member.

2. The endoscope according to claim 1, wherein the friction member moves the slide pressing member disposed to be slidable with respect to the first bearing member toward the cylindrical member due to a mating engagement between the inclined projection portions of the rotation pressing member and the inclined projection portions of the slide pressing member to increase a frictional force with the cylindrical member to give a braking force to the cylindrical member.

3. The endoscope according to claim 1, wherein each of the plurality inclined projection portions of the rotation pressing member has a flat portion at a top-most vertex position.

4. The endoscope according to claim 1, wherein each of the plurality inclined projection portions of the slide pressing member has a flat portion at a top-most vertex position.

5. The endoscope according to claim 1, wherein a disposition position of each of the plurality of positioning members correspond to a vertex position of each of the plurality inclined projection portions of the slide pressing member.

6. The endoscope according to claim 1, wherein in a state in which a flat portion of each of the inclined projection portions of the rotation pressing member is arranged on a flat portion of each of the inclined projection portions of the slide pressing member, and the braking force is regulated by causing each of the plurality of positioning members to move and abut on the regulation member.

7. The endoscope according to claim 1, wherein the second braking plate is disposed between the first braking plate and the rotation pressing member.

* * * * *